United States Patent
Zarbatany et al.

(10) Patent No.: US 7,381,210 B2
(45) Date of Patent: Jun. 3, 2008

(54) MITRAL VALVE REPAIR SYSTEM AND METHOD FOR USE

(75) Inventors: David Zarbatany, Laguna Niguel, CA (US); Tai Tieu, Fountain Valley, CA (US); Ponaka Pung, Signal Hill, CA (US); Joseph Videll, Mission Viejo, CA (US); Ken Perry, Bainbridge Island, WA (US); John Krumme, Tahoe City, CA (US); Maurice Buchbinder, La Jolla, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 673 days.

(21) Appl. No.: 10/389,721

(22) Filed: Mar. 14, 2003

(65) Prior Publication Data

US 2004/0181238 A1    Sep. 16, 2004

(51) Int. Cl.
*A61B 17/04* (2006.01)
*A61B 17/10* (2006.01)

(52) U.S. Cl. ............... 606/108; 606/139; 606/144; 606/217; 606/232; 128/898

(58) Field of Classification Search .......... 606/108, 606/194, 139, 144–151, 217, 222, 228–233; 128/898

See application file for complete search history.

(56) References Cited

U.S. PATENT DOCUMENTS

| | | | |
|---|---|---|---|
| 3,805,793 A | 4/1974 | Wright | |
| 4,350,160 A | 9/1982 | Kolesov et al. | |
| 5,080,663 A | 1/1992 | Mills et al. | |
| 5,242,456 A | 9/1993 | Nash et al. | |
| 5,258,015 A * | 11/1993 | Li et al. | 606/232 |
| 5,267,958 A | 12/1993 | Buchbinder et al. | |
| 5,330,442 A | 7/1994 | Green et al. | |
| 5,374,275 A | 12/1994 | Bradley et al. | |
| 5,403,326 A | 4/1995 | Harrison et al. | |
| 5,431,666 A * | 7/1995 | Sauer et al. | 606/139 |
| 5,443,446 A | 8/1995 | Shturman | |
| 5,458,131 A | 10/1995 | Wilk | |
| 5,474,573 A | 12/1995 | Hatcher | |
| 5,540,704 A | 7/1996 | Gordon et al. | |
| 5,569,274 A | 10/1996 | Rapacki et al. | |
| 5,573,540 A | 11/1996 | Yoon | |
| 5,575,800 A | 11/1996 | Gordon | |

(Continued)

FOREIGN PATENT DOCUMENTS

DE    197 25 739 C    4/1999

(Continued)

*Primary Examiner*—Kathleen Sonnet
*Assistant Examiner*—Kathleen Sonnett
(74) *Attorney, Agent, or Firm*—Richard B. Cates; David L. Hauser

(57) ABSTRACT

The present invention is directed to various systems for repairing tissue within the heart of a patient. The mitral valve repair system of the present invention comprises a guide catheter having a proximal end, a distal end, and at least one internal lumen formed therein, a therapy catheter capable of applying a suture to the tissue, and a fastener catheter capable of attaching a fastener to the suture. The therapy catheter and the fastener catheter are capable of traversing the internal lumen of the guide catheter. In addition, the present invention discloses various methods for repairing tissue within the heart of a patient.

10 Claims, 24 Drawing Sheets

U.S. PATENT DOCUMENTS

| | | | | |
|---|---|---|---|---|
| 5,578,044 | A | 11/1996 | Gordon et al. | |
| 5,601,574 | A | 2/1997 | Stefanchik et al. | |
| 5,609,598 | A | 3/1997 | Laufer et al. | |
| 5,662,664 | A | 9/1997 | Gordon et al. | |
| 5,669,935 | A * | 9/1997 | Rosenman et al. | 606/232 |
| 5,685,867 | A | 11/1997 | Twardowski et al. | |
| 5,695,457 | A | 12/1997 | St. Goar et al. | |
| 5,700,272 | A | 12/1997 | Gordon et al. | |
| 5,713,910 | A | 2/1998 | Gordon et al. | |
| 5,713,911 | A | 2/1998 | Racenet et al. | |
| 5,716,367 | A | 2/1998 | Koike et al. | |
| 5,741,277 | A | 4/1998 | Gordon et al. | |
| 5,741,279 | A | 4/1998 | Gordon et al. | |
| 5,766,183 | A * | 6/1998 | Sauer | 606/139 |
| 5,792,094 | A | 8/1998 | Stevens et al. | |
| 5,792,153 | A * | 8/1998 | Swain et al. | 606/144 |
| 5,810,847 | A | 9/1998 | Laufer et al. | |
| 5,814,097 | A | 9/1998 | Sterman et al. | |
| 5,836,956 | A | 11/1998 | Buelna et al. | |
| 5,839,639 | A | 11/1998 | Sauer et al. | |
| 5,849,019 | A | 12/1998 | Yoon | |
| 5,860,992 | A | 1/1999 | Daniel | |
| 5,885,238 | A | 3/1999 | Stevens et al. | |
| 5,891,159 | A | 4/1999 | Sherman et al. | |
| 5,891,160 | A | 4/1999 | Williamson et al. | |
| 5,924,424 | A | 7/1999 | Stevens et al. | |
| 5,928,224 | A | 7/1999 | Laufer | |
| 5,928,250 | A | 7/1999 | Koike et al. | |
| 5,968,059 | A | 10/1999 | Ellis et al. | |
| 5,972,020 | A | 10/1999 | Carpentier et al. | |
| 5,976,159 | A | 11/1999 | Bolduc et al. | |
| 6,004,310 | A * | 12/1999 | Bardsley et al. | 604/524 |
| 6,010,531 | A | 1/2000 | Donlon et al. | |
| 6,015,417 | A | 1/2000 | Reynolds, Jr. | |
| 6,015,427 | A | 1/2000 | Mueller et al. | |
| 6,029,671 | A | 2/2000 | Stevens et al. | |
| 6,047,700 | A | 4/2000 | Eggers et al. | |
| 6,056,760 | A | 5/2000 | Koike et al. | |
| 6,080,182 | A | 6/2000 | Shaw et al. | |
| 6,083,219 | A | 7/2000 | Laufer | |
| 6,088,889 | A | 7/2000 | Luther et al. | |
| 6,117,159 | A | 9/2000 | Huebsch et al. | |
| 6,136,010 | A * | 10/2000 | Modesitt et al. | 606/144 |
| 6,149,660 | A | 11/2000 | Laufer et al. | |
| 6,157,852 | A | 12/2000 | Selmon et al. | |
| 6,162,233 | A * | 12/2000 | Williamson et al. | 606/142 |
| 6,165,183 | A * | 12/2000 | Kuehn et al. | 606/139 |
| 6,165,204 | A | 12/2000 | Levinson et al. | |
| 6,190,357 | B1 | 2/2001 | Ferrari et al. | |
| 6,210,419 | B1 | 4/2001 | Mayenberger et al. | |
| 6,234,995 | B1 | 5/2001 | Peacock, III | |
| 6,269,819 | B1 | 8/2001 | Oz et al. | |
| 6,312,447 | B1 | 11/2001 | Grimes | |
| 6,443,922 | B1 | 9/2002 | Roberts et al. | |
| 6,461,366 | B1 | 10/2002 | Sequin | |
| 6,508,777 | B1 | 1/2003 | Macoviak et al. | |
| 6,575,971 | B2 | 6/2003 | Hauck et al. | |
| 6,582,388 | B1 | 6/2003 | Kadan et al. | |
| 6,626,930 | B1 | 9/2003 | Allen et al. | |
| 6,629,534 | B1 * | 10/2003 | St. Goar et al. | 128/898 |
| 6,629,543 | B2 * | 10/2003 | Kilgore | 137/12 |
| 6,645,205 | B2 | 11/2003 | Ginn | |
| 6,752,813 | B2 | 6/2004 | Goldfarb et al. | |
| 6,770,083 | B2 | 8/2004 | Sequin | |
| 6,875,224 | B2 | 4/2005 | Grimes | |
| 2002/0049402 | A1 | 4/2002 | Peacock et al. | |
| 2002/0107531 | A1 | 8/2002 | Schreck et al. | |
| 2003/0130571 | A1 | 7/2003 | Lattouf | |
| 2004/0044365 | A1* | 3/2004 | Bachman | 606/213 |

FOREIGN PATENT DOCUMENTS

| | | |
|---|---|---|
| EP | 0570915 A2 | 11/1993 |
| EP | 0769272 A1 | 4/1997 |
| EP | 0861632 A1 | 9/1998 |
| WO | WO 95/15715 | 6/1995 |
| WO | WO95/25468 | 9/1995 |
| WO | WO 9525468 A1 * | 9/1995 |
| WO | WO97/27807 | 8/1997 |
| WO | WO 97/27893 | 8/1997 |
| WO | WO 98/57585 | 12/1998 |
| WO | WO 99/00059 | 1/1999 |
| WO | WO 99/13777 A1 | 3/1999 |
| WO | WO 99/15223 | 4/1999 |
| WO | WO 00/03759 | 1/2000 |
| WO | WO 00/59382 | 10/2000 |
| WO | WO 00/60995 | 10/2000 |
| WO | WO 01/26557 | 4/2001 |
| WO | WO01/28432 | 4/2001 |
| WO | WO01/66018 | 9/2001 |
| WO | WO 01066018 A1 * | 9/2001 |
| WO | WO 01/95809 | 12/2001 |
| WO | WO 02/24078 | 3/2002 |
| WO | WO02/34167 | 5/2002 |

* cited by examiner

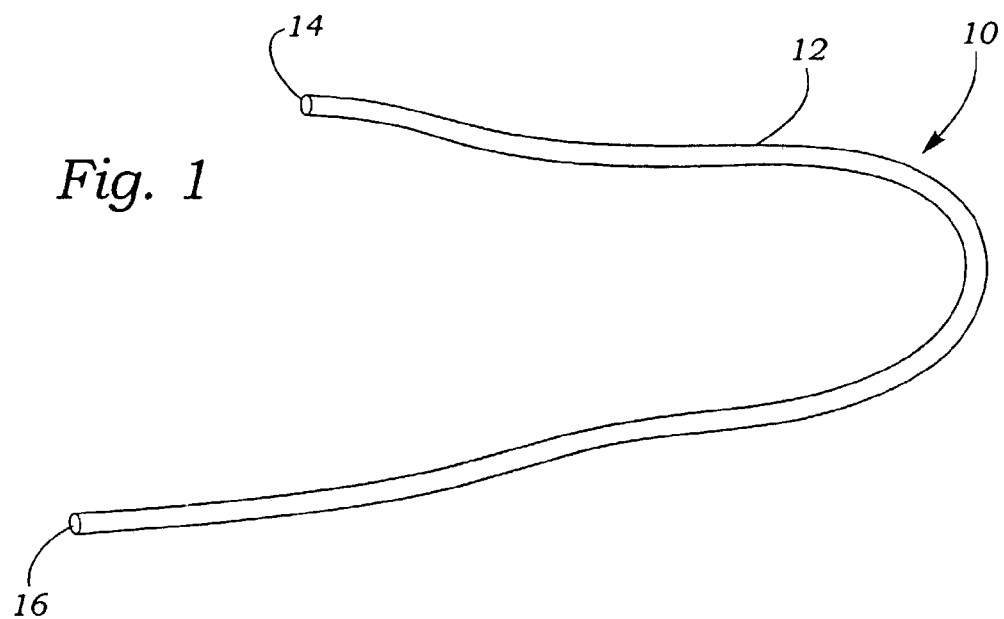
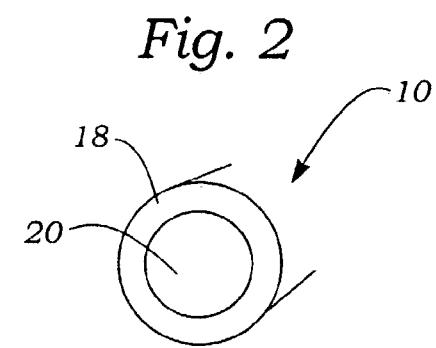 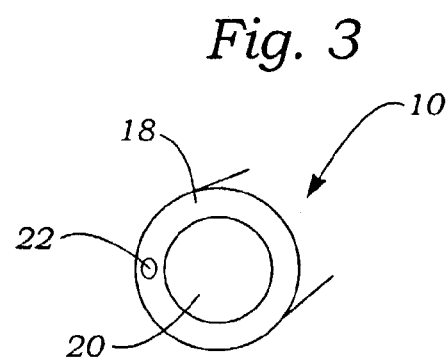
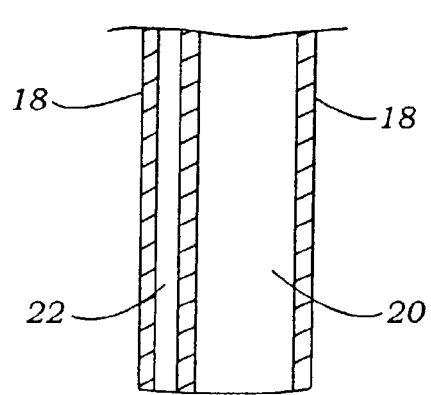

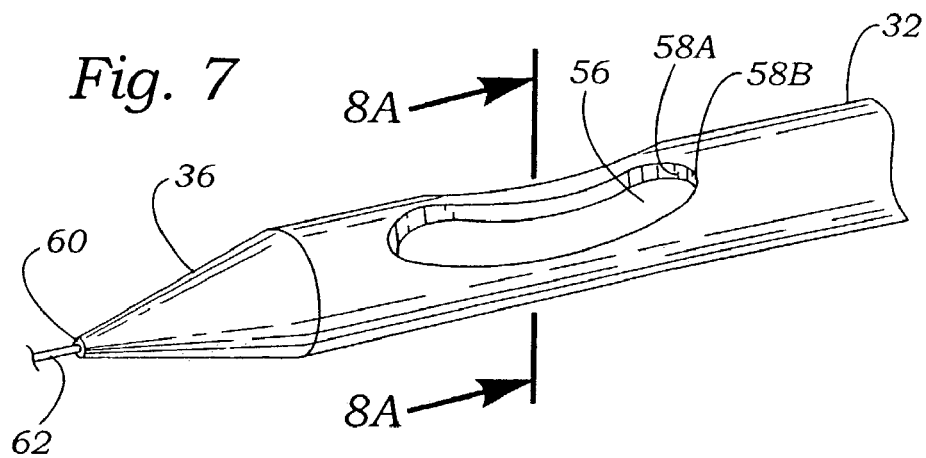
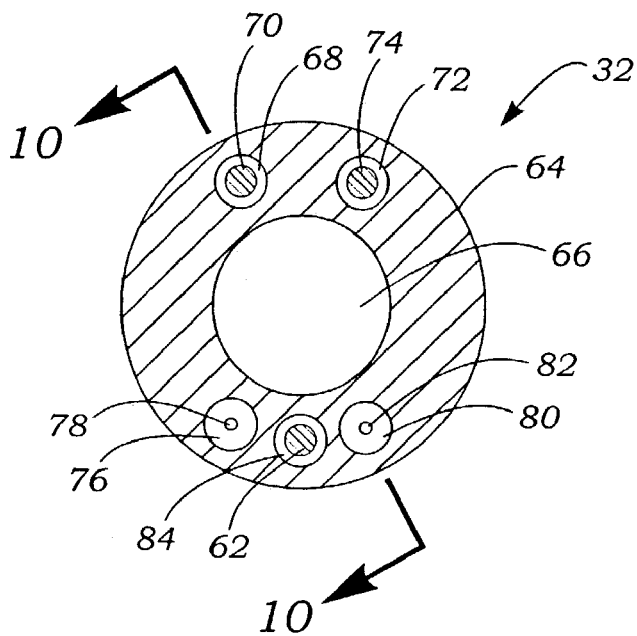
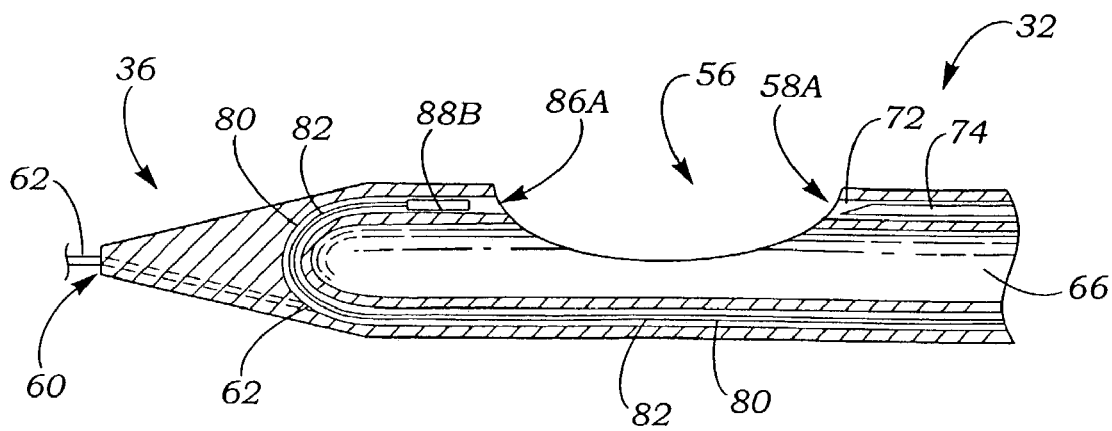

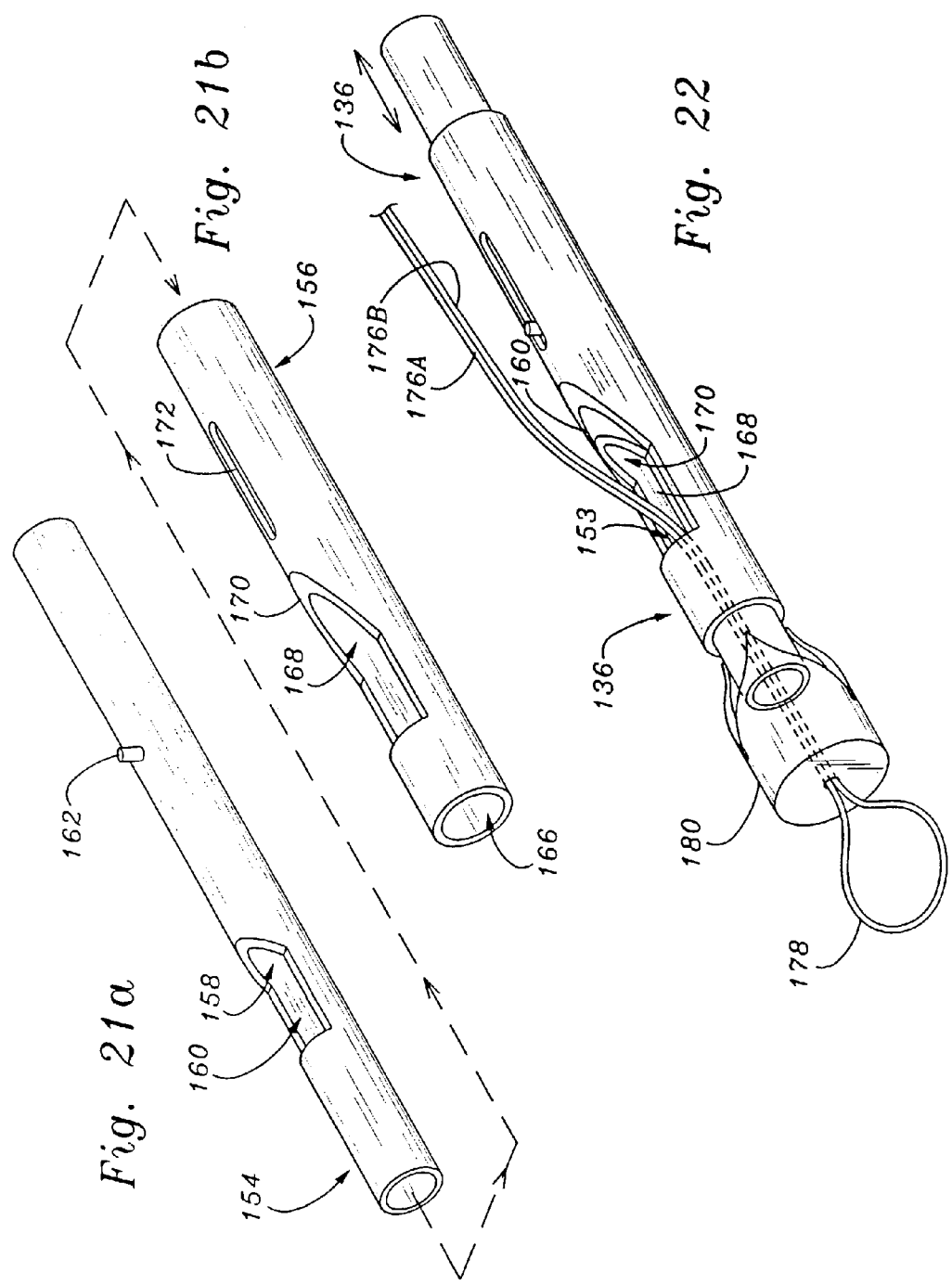

MITRAL VALVE REPAIR SYSTEM AND METHOD FOR USE

BACKGROUND OF THE INVENTION

In vertebrate animals, the heart is a hollow muscular organ having four pumping chambers: the left atrium, the left ventricle, the right atrium and the right ventricle. The atria are isolated from their respective ventricles by one-way valves located at the respective atrial-ventricular junctions. These valves are identified as the mitral (or bicuspid) valve on the left side of the heart, and tricuspid valve on the right side of the heart. The exit valves from the left and right ventricles are identified as the aortic and pulmonary valves, respectively.

The valves of the heart are positioned in valvular annuluses that comprise dense fibrous rings attached either directly or indirectly to the atrial and ventricular muscle fibers. Valve leaflets comprising flexible collagenous structures are attached to, and extend inwardly from, the annuluses to meet at coapting edges. The aortic, tricuspid and pulmonary valves each have three leaflets, while the mitral valve only has two. In normal operation, the leaflets of the mitral valve open as left ventricle dilates thereby permitting blood to flow from the left atrium into the left ventricle. The leaflets then coapt (i.e. close) during the contraction cycle of the left ventricle, thereby preventing the blood from returning to the left atrium and forcing the blood to exit the left ventricle through the aortic valve. Similarly, the tricuspid valve regulates flow from the right atrium into the right ventricle, and the pulmonary valve regulates blood exiting the right ventricle.

For a number of clinical reasons various problems with heart valves can develop. One common form of heart disease involves the deterioration or degradation of the heart valves which leads to stenosis and/or insufficiency. Heart valve stenosis is a condition in which the valve does not open properly. Insufficiency is a condition in which the valve does not close properly. Insufficiency of the mitral valve, most common because of the relatively high fluid pressures in the left ventricle, results in mitral valve regurgitation ("MR"), a condition in which blood reverses its intended course and flows "backward" from the left ventricle to the left atrium during ventricular contractions.

A number of surgical techniques have been developed to repair degraded or otherwise incompetent heart valves. A common procedure involves replacement of a native aortic or mitral valve with a prosthetic heart valve. These procedures require the surgeon to gain access to the heart through the patient's chest (or possibly percutaneously), surgically remove the incompetent native heart valve and associated tissue, remodel the surrounding valve annulus, and secure a replacement valve in the remodeled annulus. While such procedures can be very effective, there are shortcomings associated with such replacement valves. For example, the invasive nature of the implantation procedure typically results in substantial patient discomfort and requires patients to remain hospitalized for extended recovery periods. In addition, the two basic types of commercially available replacement valves, mechanical valves and tissue valves, each have shortcomings of their own. Mechanical replacement valves typically offer extended operational lifetimes, but the patient is usually required to maintain a regimen of anti-coagulant drugs for the remainder of his or her life. Tissue valves typically offer a higher degree of acceptance by the body which reduces or eliminates the need for anti-coagulants. However, the operational lifetimes of tissue valves is typically shorter than mechanical valves and thus may require a subsequent replacement(s) during the patient's lifetime.

As an alternative to prosthetic heart valve replacement, it is often preferable to remodel the native heart valve and/or the surrounding tissue. Remodeling of the valve often preserves left ventricular function better than mitral valve replacement because the subvalvular papillary muscles and chordae tendineae are preserved (most prosthetic valves do not utilize these muscles). Valvular remodeling can be accomplished by implanting a prosthetic ring (a.k.a. "annuloplasty ring") into the valve annulus to reduce and/or stabilize the structure of the annulus in order to correct valvular insufficiency. Annuloplasty rings are typically constructed of a resilient core covered with a fabric sewing material. Annuloplasty procedures can be performed alone, or they can be performed in conjunction with other procedures such as leaflet repair. Although such annuloplasty procedures have become popular and well accepted, reshaping the surrounding annulus and traditional leaflet repairs do not always lead to optimum leaflet coaptation. As a result, some patients may still experience residual mitral valve regurgitation following such annuloplasty procedures.

A recently developed technique known as a "bow-tie" repair has also been advocated for repairing insufficient heart valves, in particular the mitral valve. The mitral valve bow-tie technique involves suturing the anterior and posterior leaflets together near the middle of their coapting edges, thereby causing blood to flow through two newly formed openings. While this does reduce the volume of blood that can flow from the atrium to the ventricle, this loss is compensated by improved leaflet coaptation which reduces mitral regurgitation. This process as originally developed by Dr. Ottavio Alfieri involved arresting the heart and placing the patient on extracorporeal bypass and required invasive surgery to access and suture the leaflets together. More recently, however, some have advocated a "beating heart" procedure in which the heart is accessed remotely and remains active throughout the bow-tie procedure.

One particular method for performing a beating heart bow-tie procedure (i.e. without extracorporeal bypass) has been proposed by Dr. Mehmet Oz, of Columbia University. (See PCT publication WO 99/00059, published Jan. 7, 1999, the contents of which are incorporated herein by reference). In one embodiment of this procedure, the associated device consists of a forceps-like grasper used to grasp and hold the mitral valve leaflets in a coapted position prior to the connecting step. Since the mitral valve leaflets curve toward and slightly into the left ventricular cavity at their mating edges, the grasper device is passed through a sealed aperture in the apex of the left ventricle. The edges of the mating mitral valve leaflets are then grasped and held together, and subsequently a fastening device such as a clip or suture is utilized to fasten them. The Mehmet Oz disclosure also discloses teeth on the grasper device that are linearly slidable with respect to one another so as to permit alignment of the mitral valve leaflets prior to fastening. Since the procedure is done on a beating heart, it will be readily understood that the pressures and motions within the left ventricle and mitral valve leaflets are severe and render Dr. Oz's procedure very skill-intensive.

The bow-tie technique has proved to be a viable alternative for treating otherwise incompetent heart valves. Nonetheless, shortcomings associated with the current bow-tie procedures have been identified. Current systems typically include tissue stabilizing devices having mechanical graspers, barbed members, and vacuum devices. Often, use of these devices results in the less than optimal leaflet stabilization and fastener placement. Many of these problems arise from the fact that the surgeon is required to capture, retain and fasten the leaflets in one relatively inflexible procedure. These difficulties are compounded when the leaflets are small or calcified making them difficult to pull together, and in beating heart procedures in which the leaflets are actively functioning. In addition, the size and complexity of most current devices make minimally invasive surgical procedures more difficult, if not impossible. In light of the foregoing, there is presently a need for improved systems for stabilizing multiple tissue heart valve leaflets and placing a fastening device therebetween. More specifically, there is a present need for an improved bow-tie procedure for repairing a patient's mitral valve.

BRIEF SUMMARY OF THE INVENTION

The present invention solves the problem of effectively stabilizing at least one tissue portion in vivo. Additionally, the present invention provides a device capable of delivering a fastener to the stabilized tissue portion through a catheter from a remote insertion location.

In one aspect, the present invention is directed to a system for repairing tissue within the heart of a patient and includes a guide catheter having a proximal end, a distal end, and at least one internal lumen formed therein, a therapy catheter capable of applying at least one suture to the tissue, and a fastener catheter capable of attaching at least one fastener to the suture. The therapy catheter and the fastener catheter are capable of traversing the internal lumen of the guide catheter.

In another aspect, the present invention pertains to a system for repairing tissue within the heart of a patient and comprises a guide catheter having a proximal end, a distal end, and at least one internal lumen formed therein, a therapy catheter having at least one needle lumen in communication with at least one needle port positioned therein, at least one needle positioned within the needle lumen, and a fastener catheter having at least one fastener detachably coupled thereto. In addition, the fastener catheter includes at least one cutting member.

In yet another aspect, the present invention discloses a system for repairing tissue within the heart of a patient and includes a guide wire capable of being inserted into the patient and advanced through a circulatory pathway, a therapy catheter attachable to the guide wire and capable of applying at least one suture to the tissue, and a fastener catheter attachable to the guide wire and capable of attaching at least one fastener to the suture.

In a further aspect, the present invention pertains to a guide catheter for delivering a tissue repair device to tissue located within the heart of a patient and comprises an outer wall defining an outer wall lumen, a directing lumen capable of receiving a steering device therein and a flexible support device positioned within the outer wall lumen.

In another aspect, the present invention discloses a catheter for delivering a suture to tissue within the heart of a patient and includes an elongated body having a distal end, at least one suction recess formed on the distal end, at least one needle port located proximate to the suction recess, at least one needle lumen having at least one needle positioned therein in communication with the needle port, at least one needle receiving port having at least one needle catch located therein positioned proximate to the suction recess, and at least one actuator member in communication with the needle.

In yet another aspect, the present invention is directed to a catheter for delivering a suture to tissue within the heart of a patient and comprises an elongated body having a distal end with at least one suction recess formed thereon, at least one needle port located proximate to the suction recess, at least one needle lumen having at least one detachable needle attached to suture material positioned therein and in communication with the needle port, at least one needle receiving port located proximate to the suction recess, at least one needle trap capable of receiving the detachable needle positioned within the needle receiving port, and at least one actuator member in communication with the needle.

In yet another aspect, the present invention pertains to a device for applying a fastener to suture material attached to tissue within the body of a patient and includes a catheter body having a proximal end and a distal end, an inner body defining a suture recess and an actuation recess, and a movable sleeve defining a deployment lumen. The suture recess on the inner body is in communication with a fastener lumen capable of receiving a fastener therein. The actuation recess is in communication with an actuation lumen formed in the inner body. The deployment lumen formed in the movable sleeve is sized to receive the inner body therein and includes a cutting recess having a cutting member located proximate thereto.

In another aspect, the present invention is directed to a fastener attachable to suture material and comprises a fastener body having at least one attachment lumen formed therein and at least one engagement member attached to the fastener body wherein the engagement member is capable of engaging and retaining the suture material. The engagement member defines an engagement aperture which is in communication with the attachment lumen. The attachment lumen is capable of receiving at least one suture therein.

The present invention also discloses various methods of repairing heart valve tissue within the body of a patient. In one aspect, a method of repairing tissue within the heart of a patient is disclosed which includes advancing a guide catheter through a circulatory pathway to a location in the heart proximate to a heart valve, advancing a therapy catheter through the guide catheter to the heart valve, stabilizing a first leaflet with the therapy catheter, deploying a first suture into the stabilized first leaflet, disengaging the first leaflet from the therapy catheter while leaving the first suture attached thereto, stabilizing a second leaflet with the therapy catheter, deploying a second suture into the second leaflet, disengaging the second leaflet from the therapy catheter while leaving the second suture attached thereto, and joining the first and second leaflets by reducing the distance between the first and second sutures.

An alternate method of repairing tissue within the heart of a patient is disclosed and comprises advancing a guide catheter through a circulatory pathway to a location in the heart proximate to a heart valve, advancing a therapy catheter through the guide catheter to the heart valve, stabilizing a first leaflet with the therapy catheter, deploying a first suture into the stabilized first leaflet, disengaging the first leaflet from the therapy catheter while leaving the first suture attached thereto, stabilizing a second leaflet with said therapy catheter, deploying a second suture into the second leaflet, disengaging the second leaflet from the therapy catheter while leaving the second suture attached thereto, and removing the therapy catheter from the guide catheter. Thereafter, a fastener catheter is positioned over the first and second suture and advanced through the guide catheter to the heart valve. Once positioned, the first and second leaflets are joined by reducing the distance between the first and second sutures and a fastener is deployed from the fastener catheter.

Other objects, features, and advantages of the present invention will become apparent from a consideration of the following detailed description.

BRIEF DESCRIPTION OF THE DRAWINGS

The apparatus of the present invention will be explained in more detail by way of the accompanying drawings, wherein:

FIG. 1 shows a perspective view of an embodiment of the guide catheter of the present invention;

FIG. 2 shows a cross-sectional view of an embodiment of the, guide catheter of the present invention;

FIG. 3 shows a cross-sectional view of an alternate embodiment of the guide catheter of the present invention;

FIG. 4 shows a cross-sectional view of the embodiment of the guide catheter shown in FIG. 3;

FIG. 7 shows an perspective view of an embodiment of the elongated body of the present invention having a suture attachment tip attached thereto;

FIG. 8A shows a cross-sectional view of an embodiment of the elongated body of the present invention;

FIG. 10 shows a side cross-sectional view of the embodiment of the elongated body shown in FIG. 9 prior to actuation;

FIGS. 21a and 21b show a perspective view of the components of the fastener tip of the present invention;

FIG. 22 shows a perspective view of the fastener tip of the present invention having a fastener attached thereto;

DETAILED DESCRIPTION OF THE INVENTION

Figure 5:
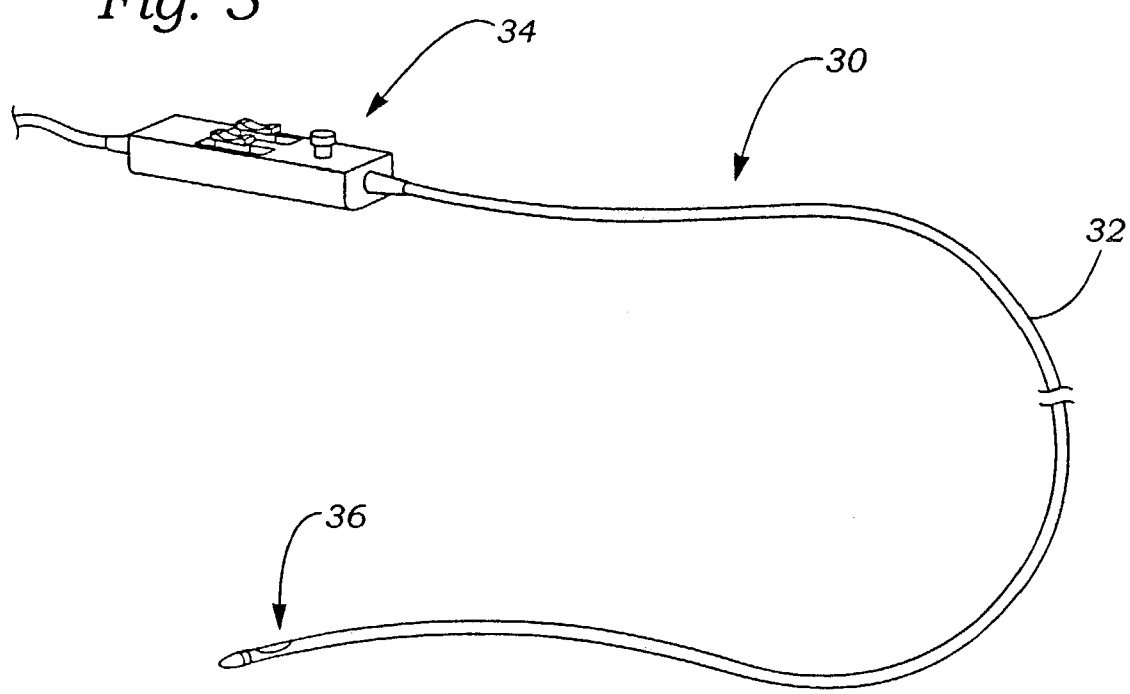
FIG. 5 shows a perspective view of an embodiment of the therapy catheter of the present invention.

Disclosed herein is a detailed description of various embodiments of the present invention. This description is not to be taken in a limiting sense, but is made merely for the purpose of illustrating the general principles of the invention. The overall organization of the detailed description is for the purpose of convenience only and is not intended to limit the present invention.

The mitral valve repair system of the present invention is designed for use in a surgical treatment of bodily tissue. As those skilled in the art will appreciate, the exemplary mitral valve repair system disclosed herein is designed to minimize trauma to the patient before, during, and subsequent to a minimally invasive surgical procedure while providing improved tissue stabilization and enhanced placement of a fastening device thereon. The mitral valve repair system of the present invention includes a guide catheter capable of being introduced into body of a patient and advanced to an area of interest, a therapy catheter capable of traversing or otherwise engaging the guide catheter and applying a suture to a repair site, and a fastener catheter capable of applying a fastening device to the attached suture. While the guide catheter, therapy catheter, and fastener catheter cooperatively enable a surgeon to deliver a suture to a repair site in vivo, the various components of the present invention may be used individually. For example, the therapy catheter, the fastener catheter, or both may be coupled to a guidewire and advanced to a repair site in vivo without the use of the guide catheter. The mitral valve repair system of the present invention is useful in repairing dysfunctional mitral valve tissue by stabilizing discreet valvular tissue pieces and deploying a fastening device therethrough. However, the mitral valve repair system may be used to repair tissue throughout a patient's body as desired. For example, the present invention may also be used to repair arterial septal defects (ASD), ventricular septal defects (VSD), and defects associated with patent foramen ovale (PFO).

FIGS. 1-4 show various illustrations of the guide catheter of the present invention. As shown in FIG. 1, the guide catheter 10 comprises a guide body 12 having a proximal end 14 and a distal end 16. Those skilled in the art will appreciate that the guide catheter 10 of the present invention may be manufactured from a variety of materials, including, without limitation, various plastics, thermoplastics, silicones, elastomers, ceramics, composite materials, or various combinations of the aforementioned materials. In addition, the guide catheter 10 may be manufactured in various lengths and widths as desired by the user. FIGS. 2-4 show various embodiments of the guide catheter 10. As shown in FIG. 2, the guide catheter 10 includes an outer wall 18 defining at least one internal lumen 20. FIGS. 3-4 illustrate alternate embodiments wherein the outer wall 18 defines an internal lumen 20 and includes at least one directing lumen 22 formed therein. The directing lumen 22 is sized to receive a guidewire (not shown) or steering device (not shown) therein. In another embodiment, at least one flexible support structure such as a coiled wire support (not shown) may be embedded within the outer wall 18 of the guide catheter 10.

FIG. 5 shows a perspective view of an embodiment of the therapy catheter 30 of the present invention. As shown in FIG. 5, the therapy catheter 30 includes an elongated body 32 having a therapy device handle 34 located at the proximal end and a suture attachment tip 36 located at the distal end. Like the guide body 12 of the guide catheter 10, the elongated body 32 may be manufactured in a variety of shape, sizes, lengths, widths, and biologically-compatible materials as desired.

Figure 6:
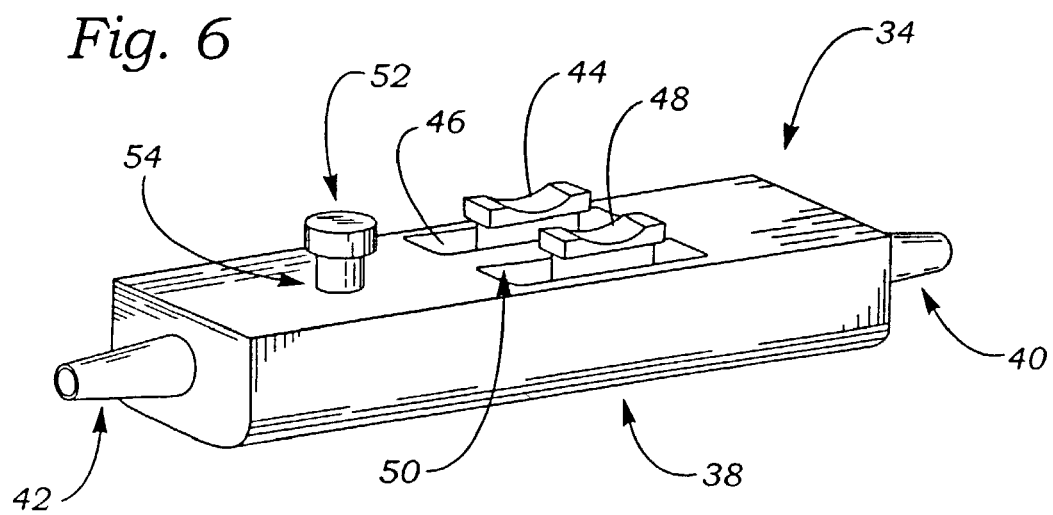
FIG. 6 shows an embodiment of the therapy device handle of the present invention.

FIG. 6 shows a more detailed illustration of the therapy device handle 34 of the present invention. As shown, the therapy device handle 34 comprises a handle body 38 having at least a suction connector 40 and a elongated body receiver 42 attached thereto. The suction connector 40 is capable of coupling to a vacuum source (not shown). The elongated body receiver 42 is capable of receiving the elongated body 32 (FIG. 5) thereon. A first actuator 44 is located within a first actuator recess 46 formed on the handle body 38. Similarly, a second actuator 48 is positioned within a second actuator recess 50 formed in the handle body 38. As shown in FIG. 6, a suction actuator 52, configured to open or close the fluid path between suction connector 40 and elongated body receiver 42, may be located within a suction actuator recess 54 proximal to the first and second actuators 44, 48.

FIGS. 7-10 show various illustrations of the elongated body 32 and the suture attachment tip 36 of the present invention. As shown in FIG. 7, the elongated body 32 includes a suction recess 56 having a first needle port 58A and a second needle port 58B located proximate thereto. The elongated body 32 or the suture attachment tip 36 may include a guidewire port 60 capable of receiving a guidewire 62. FIG. 8A shows a cross sectional view of the elongated body 32. As shown, the elongated body 32 comprises an outer wall 64 defining a suction lumen 66. The suction lumen 66 is in fluid communication with the suction recess 56 (FIG. 7) and the vacuum source (not shown) attached to the suction connector 40 located on the therapy device handle 34 (FIG. 6). A first needle lumen 68 having a first needle 70 located therein may be formed in or otherwise positioned proximate to the outer wall 64 of the elongated body 32. Similarly, a second needle lumen 72 having a second needle 74 located therein may be formed in or otherwise positioned proximate to the outer wall 64 of the elongated body 32. The first and second needles 70, 74 are coupled to or otherwise in communication with the first and second actuators 44, 48 located on the therapy device handle 34 (FIG. 6). The forward and rearward movement of the first and second actuators 44, 48 results in the longitudinal movement of the first and second needles 70, 74 thereby permitting the first and second needles, 70, 74 to extend from and retract into the first and second needle lumens 68, 72. Those skilled in the art will appreciate that the first and second needles 70, 74 may be capable of individual or simultaneous movement. A first suture lumen 76 having a first suture 78 located therein and a second suture lumen 80 having a second suture 82 located therein may be formed within or located proximate to the outer wall 64 of the elongated body 32. Of course one of skill in the art will recognize that references herein to "sutures" include not just traditional suture material, but also any material of sufficient length and flexibility to accomplish the purposes of this tissue repair system. In one embodiment, a guidewire lumen 84 sized to receive guidewire 62 therein may be positioned within or proximate to the outer wall 64 of the elongated body 32 and may be in communication with the guidewire port 60 formed on the suture attachment tip 36.

Figure 8B:
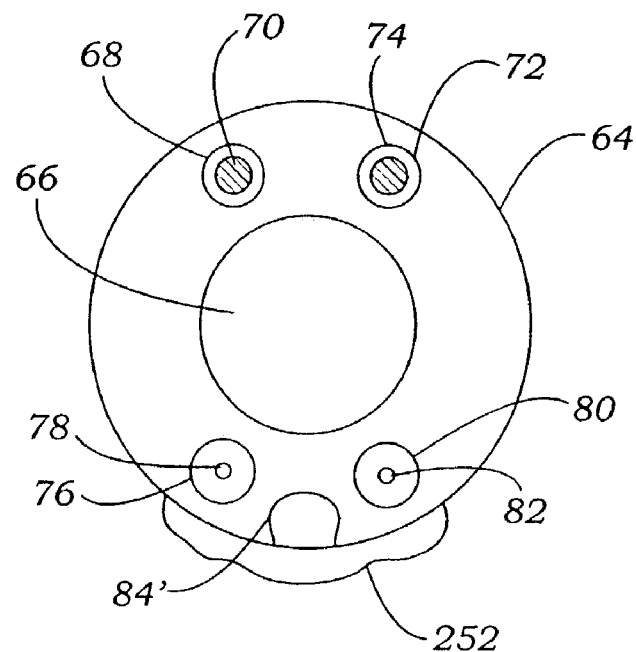
FIG. 8B shows a cross sectional view of an alternate embodiment of the elongated body of the present invention.
Figure 8C:
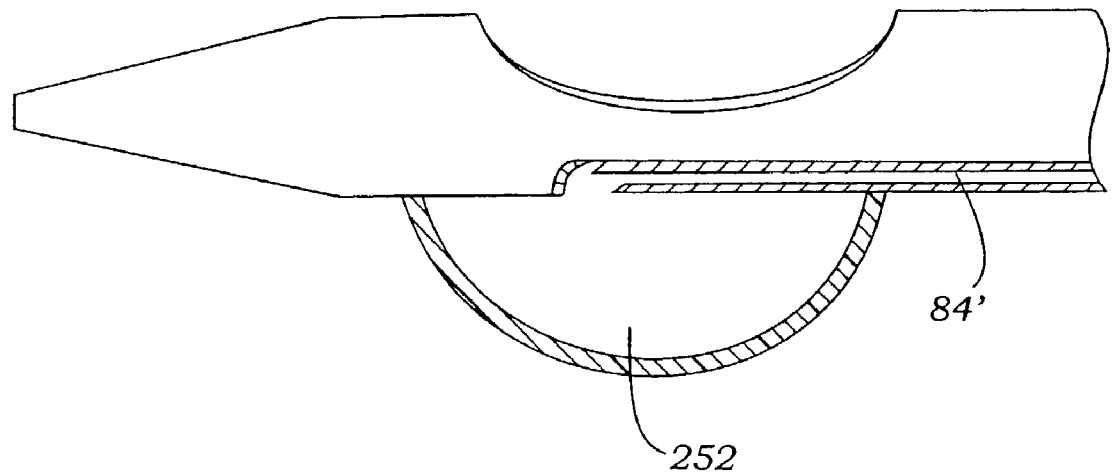
FIG. 8C shows a side cross-sectional view of the embodiment of the elongated body shown in FIG. 8B.

FIGS. 8B-8C show various illustrations of an alternate embodiment of the present invention, wherein an inflatable positioning balloon 252 is positioned on the outer wall 64 of the elongated body 32. As shown, the inflatable positioning balloon 252 is in fluid communication with an inflation lumen 84' positioned within the elongated body 32. The inflation lumen 84' may be in fluid communication with an inflation source in ways known to those skilled in the art and may be attached to or otherwise in communication with the therapy device handle 34 (FIG. 5), thereby permitting the position of the therapy catheter 30 to be manipulated without using a guidewire. Moreover, the positioning balloon 252 can be used to hold the therapy device steady once in position.

Figure 9:
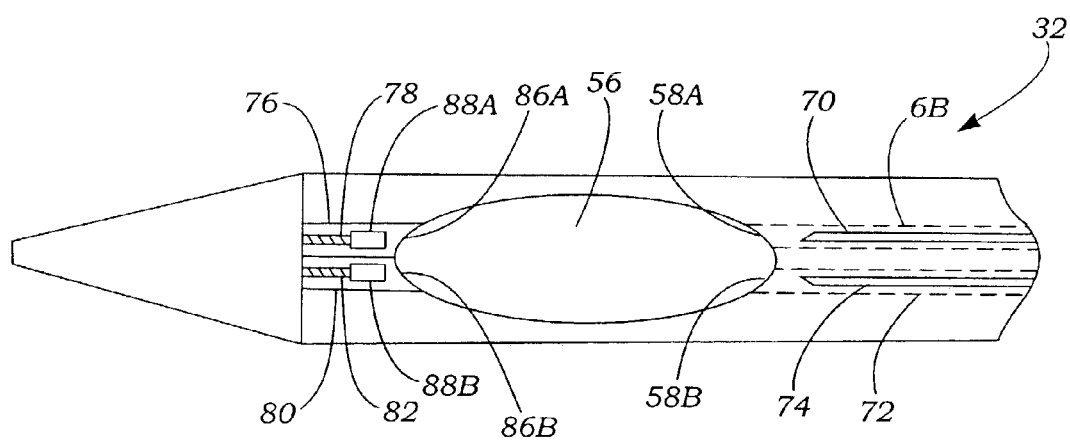
FIG. 9 shows a top cross-sectional view of an embodiment of the elongated body of the present invention.

FIGS. 9-10 show various illustrations of the present invention prior to use. As shown, a first needle receiving port 86A may be positioned within or proximate to the suction lumen 56 co-aligned with and opposing the first needle port 58A. Similarly, a second needle receiving port 86B may be positioned within or proximate to the suction lumen 56 co-aligned with and opposing the second needle port 58B. The first needle receiving port 86A is in communication with the first suture lumen 76 and contains at least a first needle catch 88A attached to the first suture 78 therein. Likewise, the second needle receiving port 86B is positioned proximate to the suction recess 56 opposing the second needle port 58B. The second needle receiving port 86B is in communication with the second suture lumen 80 and contains a second needle catch 88B attached to the second suture 82 therein.

Figure 11:
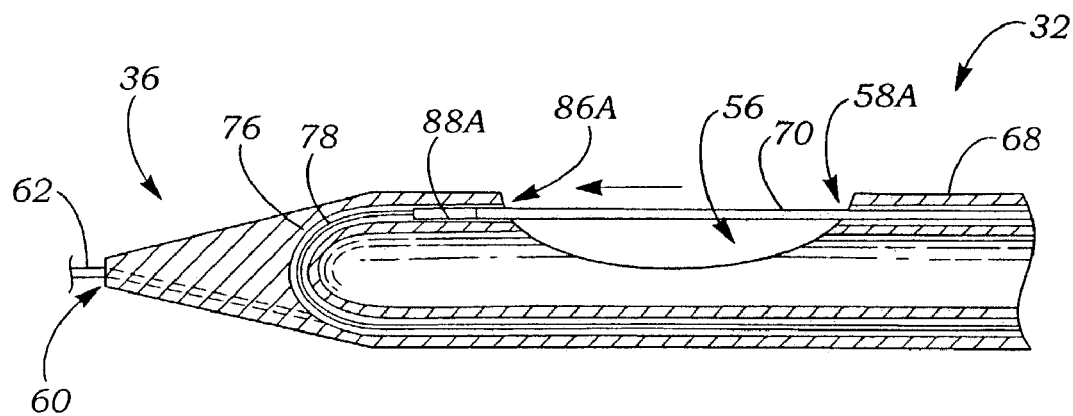
FIG. 11 shows a side cross-sectional view of an embodiment of the elongated body shown in FIG. 10 during actuation.
Figure 12:
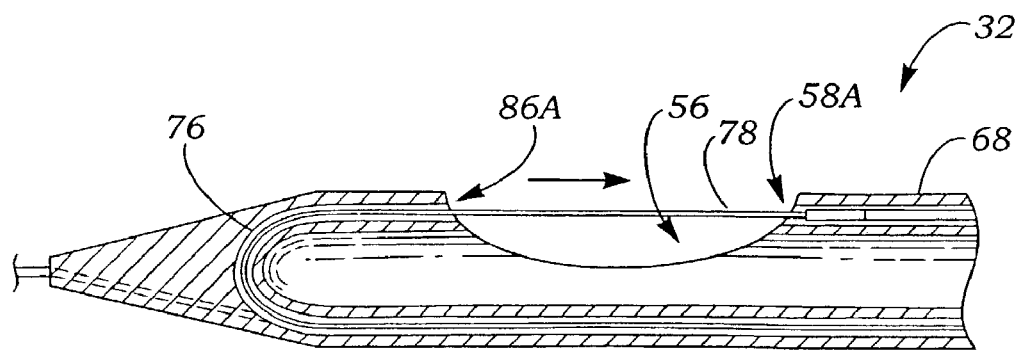
FIG. 12 shows a side cross-sectional view of an embodiment of the elongated body shown in FIG. 10 following actuation.

FIGS. 11-12 show an embodiment of the therapy catheter of the present invention during various stages of use. As shown in FIG. 11, forward movement of the first actuator 44 within the first actuator recess 46 (FIG. 6) results in the first needle 70 advancing through the first needle port 58A and traversing the suction recess 56. Continued actuation of the first actuator 44 results in the first needle 70 advancing through the first needle receiving port 86A and engaging the first needle catch 88A positioned within the first suture lumen, 76. The first needle catch 88A engages and is retained on the first needle 70. The user may then retract the first needle 70, thereby pulling the first suture across the suture recess 56. To retract the first needle 70, the user rearwardly moves the first actuator 44. As shown in FIG. 12, the first needle 70 having the first needle catch 88A attached thereto is retracted through the first needle receiving port 86A, traverses the suction recess 56, and enters the first needle lumen 68. through the first needle port 58A. FIG. 12 shows the first suture 78 traversing the suction recess 56.

Figure 13:
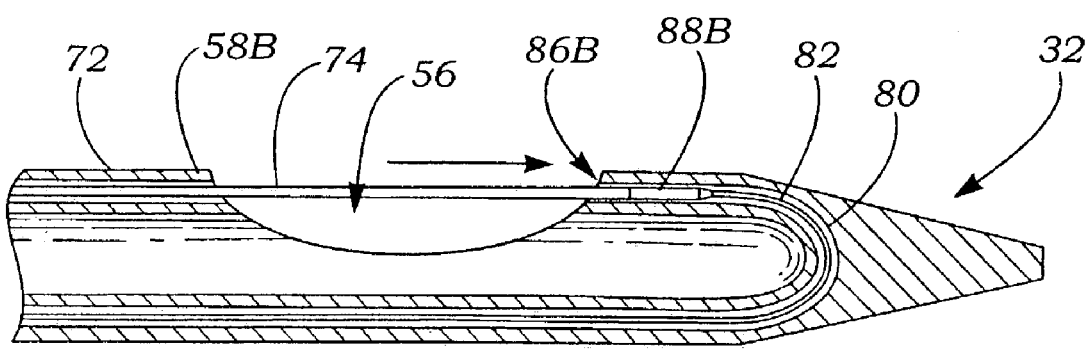
FIG. 13 shows another side cross-sectional view of an embodiment of the elongated body shown in FIG. 10 during actuation.
Figure 14:
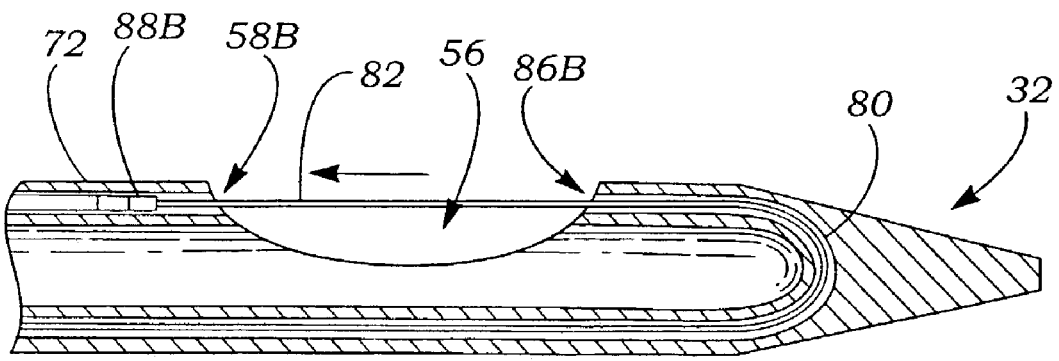
FIG. 14 shows another side cross-sectional view of an embodiment of the elongated body shown in FIG. 10 following actuation.

Similarly, as shown in FIG. 13, forward movement of the second actuator 48 (FIG. 6) results in the second needle 74 advancing through exiting the second needle port 58B and traversing the suction recess 56. Like the actuation process described above, the continued actuation of the second actuator 48 results in the second needle 74 advancing through the second needle receiving port 86B and engaging the second needle catch 88B positioned within the second suture lumen 80. The second needle catch 88B is then engaged and retained on the second needle 74. Thereafter, the user may retract the second needle 74 thereby pulling the second suture across suture recess second needle port 58B. To retract the second needle 74, the user rearwardly moves the second actuator 48. As shown in FIG. 14, the second needle 74 having the second needle catch 88B attached thereto is retracted through the second needle receiving port 86B, traverses the suction recess 56, and enters the second needle lumen 72 through the second needle port 58B. The second suture 82, which is attached to the second needle catch 88B, thus traverses the suction recess 56.

Figure 15:
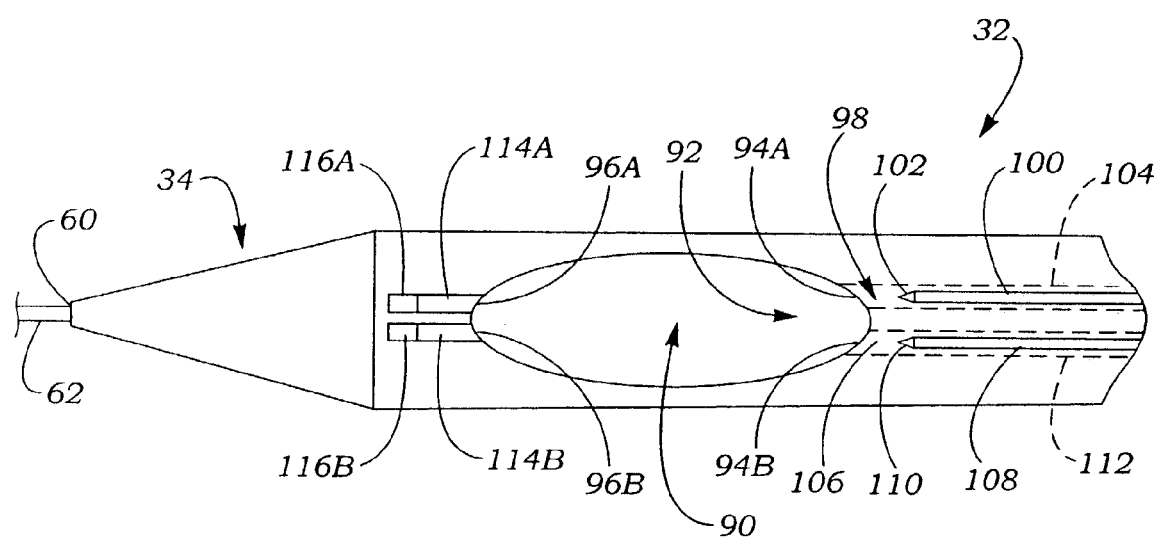
FIG. 15 shows a top cross-sectional view of an alternate embodiment of the elongated body of the present invention.

FIG. 15 illustrates an alternate embodiment of the present invention. As shown, the elongated body 32 includes a suction recess 90 formed thereon which is in fluid communication with a suction lumen 92 formed therein which in turn is in communication with a vacuum source (not shown) attached to the suction connector 40 (FIG. 6). First and second needle ports 94A, 94B, respectively, are positioned within or proximate to the suction recess 90. Similarly, first and second needle receiving ports 96A, 96B, respectively, are positioned within or proximate to the suction recess 90 and are co-aligned with and opposed to the first and second needle ports 94A, 94B. The first needle port 94A communicates with a first needle lumen 98. A first deployment rod 100 having a first detachable needle 102 attached thereto is located within the first needle lumen 98. The first detachable needle 102 is coupled to a first suture 104 located within the first needle lumen 98. Similarly, the second needle port 94B communicates with a second needle lumen 106. A second deployment rod 108 having a second detachable needle 110 attached thereto is located within the second needle lumen 106. The second detachable needle 110 is coupled to a second suture 112 located within the second needle lumen 106. The first needle receiving port 96A leads to a first needle trap lumen 114A formed in or positioned proximate to suction recess 90. A first needle trap 116A capable of receiving and retaining the first detachable needle 102 therein is positioned within the first needle trap lumen 114A. Similarly, the second needle receiving port 96B leads to a second needle trap lumen 114B formed in or positioned proximate to the suction recess 90. Like the first needle trap 116A, a second needle trap 116B capable of receiving and retaining the second detachable needle 110 therein is positioned within the second needle trap lumen 114B.

Figure 16:
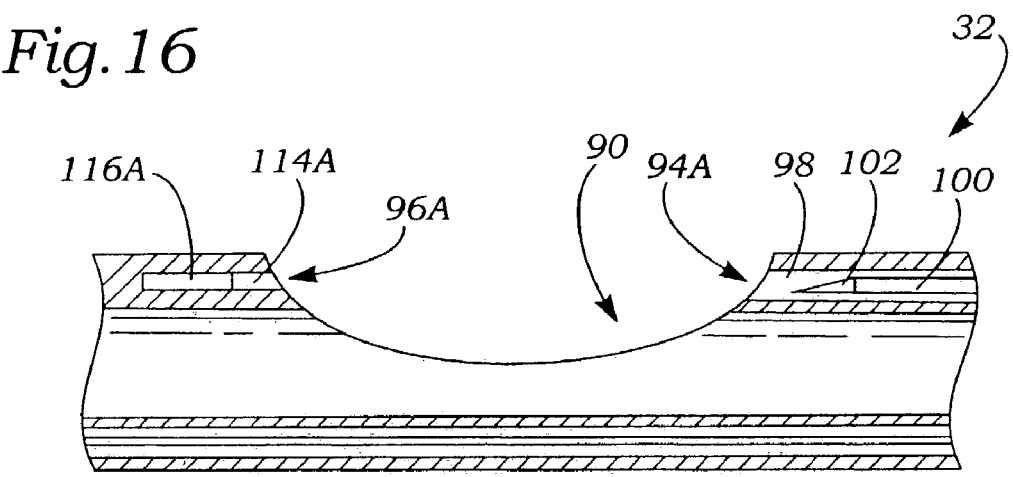
FIG. 16 shows a side cross-sectional view of the embodiment of the elongated body shown in FIG. 15 prior to actuation.
Figure 17:
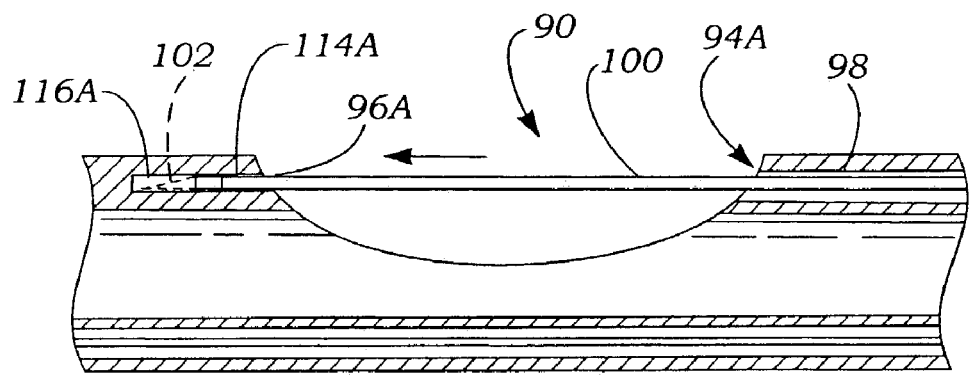
FIG. 17 shows a side cross-sectional view of an embodiment of the elongated body shown in FIG. 15 during actuation.
Figure 18:
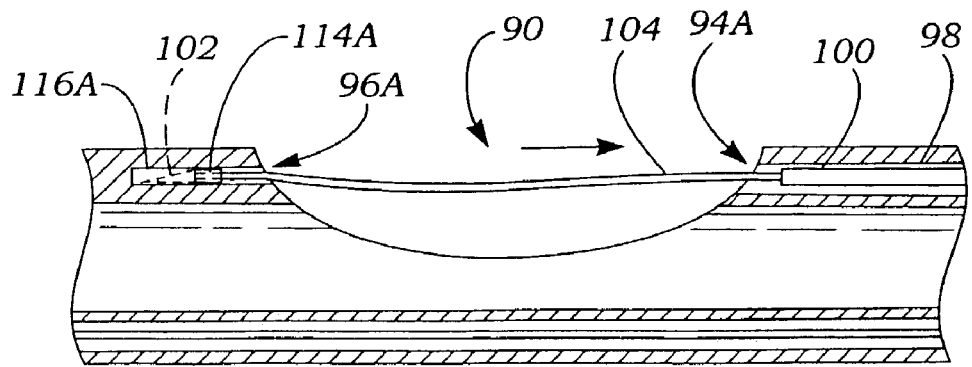
FIG. 18 shows a side cross-sectional view of an embodiment of the elongated body shown in FIG. 15 following actuation.

FIGS. 16-18 show the embodiment of FIG. 15 during use. Forward movement of the first actuator 44 results in first needle rod 100 extending from first needle lumen 98. FIG. 17 shows the first needle rod 100 with a first detachable needle 102 attached thereto extended through the first needle port 94A traversing the suction recess 90, and entering into the first needle trap lumen 114A through the first needle receiving port 96A. The first detachable needle then engages the first needle trap 116A. Thereafter, the first needle rod 100 is retracted into the first needle lumen 98, thereby leaving first detachable needle 102 in first needle trap 116A. To retract the first needle rod 100, the user moves the first actuator 44 a rearward direction which causes the first needle rod 100 to retract into the first needle lumen 98. FIG. 18 shows the first needle rod 100 retracted into the first needle lumen 98. As a result, the first suture 104 which is attached to the first detachable needle 102 traverses the suction recess 90. Those skilled in the art will appreciate that a second needle (not shown) may be deployed in a similar manner.

Figure 19:
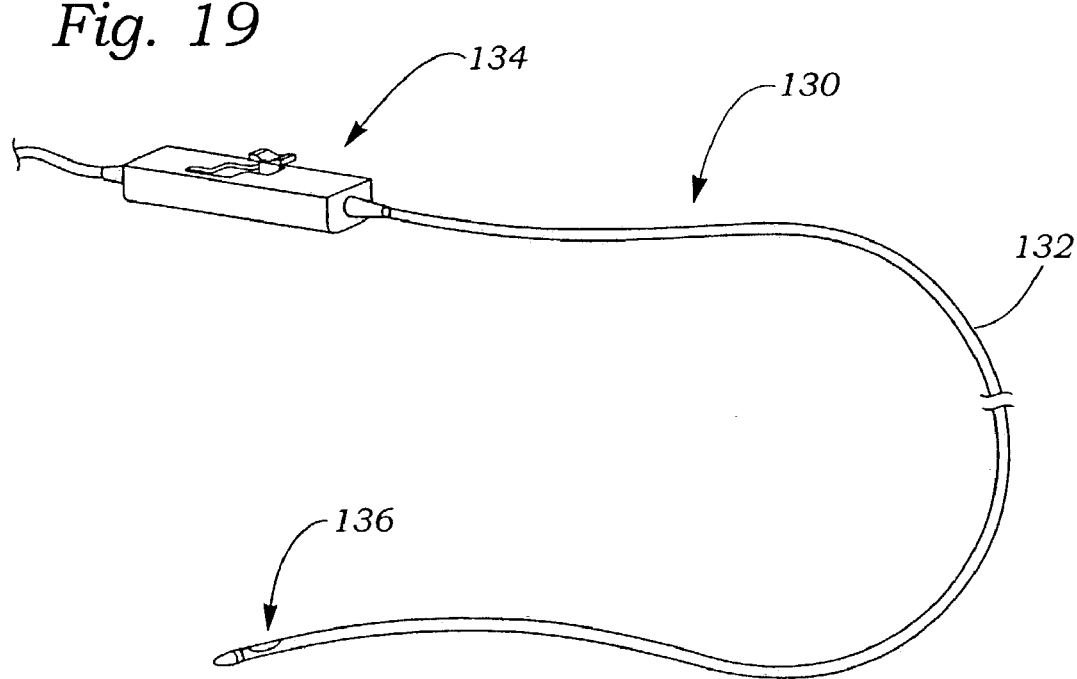
FIG. 19 shows a perspective view of an embodiment of the fastener catheter of the present invention.
Figure 20:
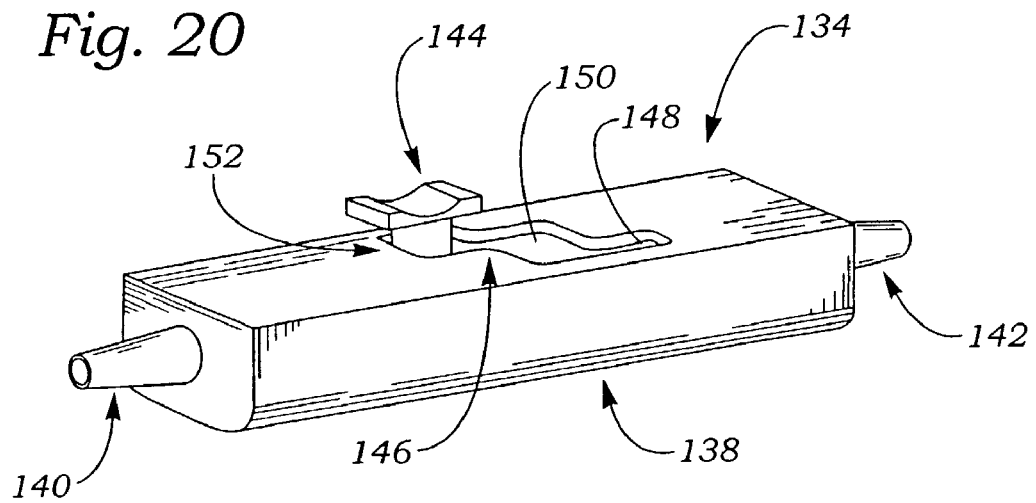
FIG. 20 shows an embodiment of the fastener catheter handle of the present invention.

FIGS. 19-21 show various illustrations of the fastener catheter of the present invention. As shown in FIG. 19, the fastener catheter 130 comprises a fastener catheter body 132 having a fastener catheter handle 134 attached at the proximal end and a fastening tip 136 at the distal end. The fastener catheter 130 may be manufactured in a variety of shapes, sizes, lengths, widths, and biologically-compatible materials as desired.

FIG. 20 shows a more detailed illustration of a preferred fastener catheter handle 134 of the present invention. As shown, the fastener catheter handle 134 comprises a fastener handle body 138 having an auxiliary connector 140 and a fastener body receiver 142 attached thereto. The auxiliary connector 140 may be capable of coupling to a variety of devices including, for example, a vacuum source or a visualization device. The fastener body connector 142 is capable of receiving and coupling to the fastener catheter body 132 (FIG. 19). A fastener actuator 144 may be positioned within a fastener actuator recess 146 formed on the fastener handle body 138. The fastener actuator 144 positioned within the fastener actuator recess 146 may be capable of being positioned in three distinct locations. For example, in a non-actuated condition, the fastener actuator 144 may be located in a first position 148. Thereafter, the user may partially actuate the fastener catheter 130 by positioning the fastener actuator 144 in a second position 150, thereby deploying a fastening device (not shown) from the fastener catheter 130 (FIG. 19). The user may then fully actuate the fastener catheter 130 by moving the fastener actuator 144 to a third position 152 within the fastener actuator recess 146, thereby actuating a cutting member (discussed below) located on or proximate to the fastening tip 136.

FIGS. 21*a* and 21*b* illustrate, in exploded fashion, pieces of fastening tip 136. An inner body 154 includes a suture recess 160 formed in the side thereof, which in turn is in communication with an internal fastener lumen 158. Inner body 154 also includes a pin 162 extending radially outward therefrom. Sleeve 156 comprises an axial deployment lumen 166 of sufficient diameter to receive inner body 154 therein. Sleeve 156 also comprises a cutting recess 168 formed in an axial side thereof and a cutting member 170 on a proximal edge of cutting recess 168. Slot 172 extends parallel to the axis of the deployment lumen 166 and may extend radially through to fastener lumen. Pin recess 172 receives pin 162 in sliding relation.

Figure 23:
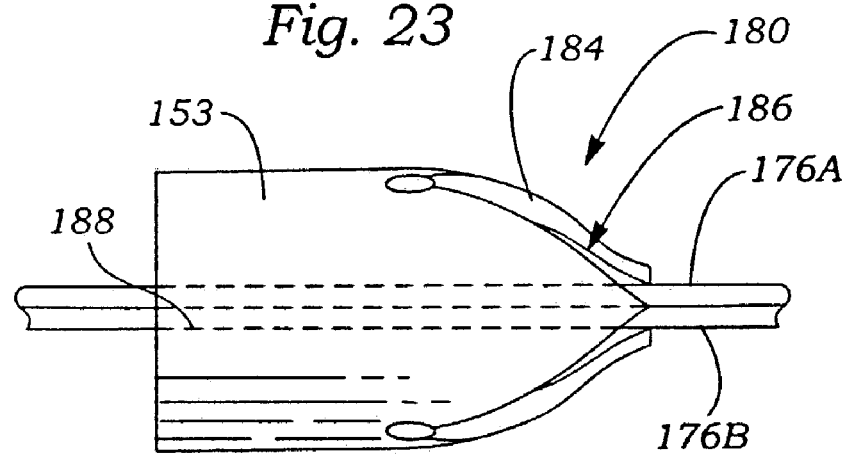
FIG. 23 shows a side view of an embodiment of the fastener of the present invention.
Figure 24:
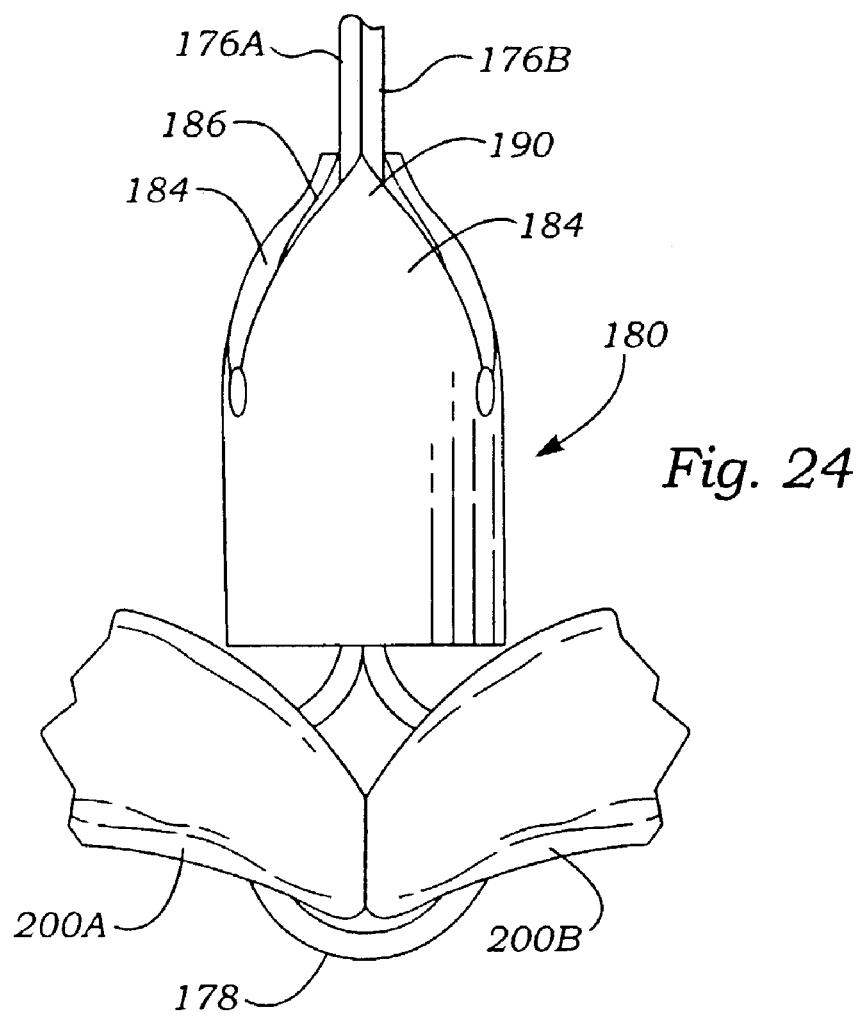
FIG. 24 shows a side view of the fastener of the present invention attached to suture material.

FIGS. 23-24 illustrate fastener 180 of the present invention. Fastener 180 may be manufactured from a variety of materials including, for example, Nickel-Titanium alloys, shape-memory alloys, stainless steel, titanium, various plastics, and other biologically-compatible materials. Fastener 180 has an internal attachment lumen 188 extending axially therethrough and one or more engagement member(s) 184 formed on an end thereof. Between the engagement members is defined engagement aperture 186 which is in communication with internal attachment lumen 188. Internal attachment lumen 188 and engagement aperture 186 are sized to receive a first suture lead 176A and a second suture lead 176B therein. Prior to deployment, engagement member(s) 184 are deflected radially away from the axis of the fastener 180 such that engagement aperture 186 has a relative large first diameter sufficient to permit suture leads 176A and 176B to slide therethrough. Upon deployment, i.e, after the suture leads 176A and 176B have been retracted, engagement members 184 are deflected or permitted to spring back toward the axis of the device such that the engagement aperture 186 assumes a second smaller diameter compressing and securing suture leads 176A and 176B in place. Preferably the engagement member(s) 184 tend to spring toward a natural position at the axis of fastener 180. FIG. 24 shows the fastener 180 in the deployed configuration in which a suture loop 178 has passed through two discreet tissue portions 200A, 200B and suture leads 176A, 176B are secured in fastener 180. Each engagement member (s) 184 may further include a pointed tip 190 which, when the engagement member(s) are in the deployed position, engages and further restricts movement of the suture leads 176A, 176B.

An operational fastening tip 136 with fastener 180 attached thereto and ready for deployment can be seen in FIG. 22. Inner body 154 has been placed inside sleeve 156 such that suture recess 160 is in alignment with cutting recess 168. Pin 172 is in slidable communication with slot 162 thereby permitting relative linear motion, but preventing relative rotational motion, between inner body 154 and sleeve 156. Fastener 180 has been placed on the end of the fastening tip 136 by deflecting the engagement members 184 radially outward until they can be placed around the outer circumference of the inner body 154. Accordingly, the fastener is secured to the end of inner body 154 by means of the frictional engagement between the engagement members 184 and the outer surface of inner body 154. Suture loop 178 extends from the fastener 180. Suture leads 176A and 176B extend through the internal attachment lumen 188, through engagement aperture 186, exit the side of inner body 154 through suture recess 160, and exit the side of sleeve 156 through cutting recess 168.

Deployment of the fastener is a two step process. Once suture 178 has been secured through one or more tissue segments, the fastener tip 136 is coaxed toward the tissue and the suture leads 176A and 176B are pulled away from the tissue until the suture loop is sufficiently cinched around the target tissue. Sleeve 156 is then held in place adjacent the tissue while the inner body 154 is pulled axially away. This causes sleeve 156 to push (i.e. slide) fastener 180 off the outer surface of the inner body 154. When fastener 180 has been completely removed from inner body 154 engagement members 184 spring axially inward thereby reducing the diameter of engagement aperture 186 and securing suture leads 176A and 176B. The second deployment step, cutting suture leads 176A and 176B, is accomplished when the inner body 154 is pulled sufficiently through sleeve 156 that the suture leads are pinched between the trailing edge of suture recess 160 and cutting member 170 and ultimately cut by cutting member 170.

Remote deployment of fastener 180 is accomplished by attaching inner body 154 to fastener actuator 144, and attaching sleeve 156 to the fastener catheter handle 134. Thus, axial movement of the fastener actuator 144 relative to the handle 134 causes similar relative movement between inner body 154 and sleeve 156. For example, in the non-actuated position 148 (see FIG. 20) the distal end of inner body 154 will extend from sleeve 156 a sufficient distance to hold fastener 180 thereon. In the second position 150 the inner body 154 will have been withdrawn into sleeve 156 a sufficient distance to deploy the fastener 180, and in the third position 152 the inner body 154 will have been withdrawn a sufficient distance to cut the suture leads 176A and 176B.

The present invention also discloses various methods of using the disclose mitral valve repair system to repair discreet tissue portions in vivo. The following paragraphs describe methods of repairing a dysfunctional mitral valve, though those skilled in the art will appreciate that the present invention and procedure may be adapted for use on other valves or in other procedures requiring the attachment of two or more pieces of tissue.

Figure 25:
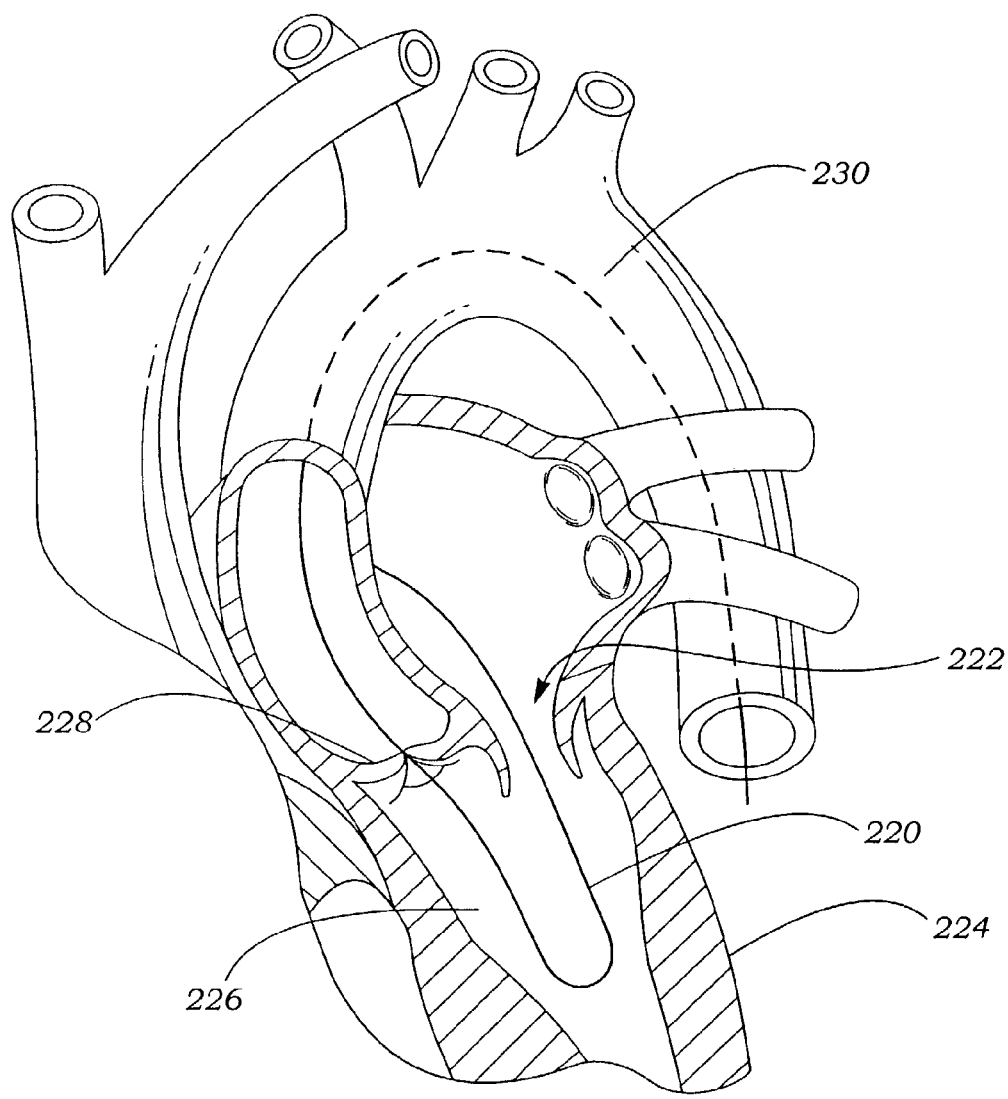
FIG. 25 shows a perspective view of a guidewire traversing the mitral valve within a heart.

To repair a dysfunctional or otherwise incompetent heart valve, a guidewire capable of traversing the circulatory system and entering the heart of the patient is introduced into the patient through an endoluminal entry point. For example, the endoluminal entry point may be formed in a femoral vein or right jugular vein. Thereafter, the guidewire is advanced through the circulatory system, eventually arriving at the heart. The guidewire is directed into the right atrium, traverses the right atrium and is made to puncture with the aid of a tran-septal needle or pre-existing hole, the atrial septum, thereby entering the left atrium. As shown in FIG. 25, the guidewire 220 may then be advanced through the mitral valve 222 and into the left ventricle 226. The guidewire 220 traverses the aortic valve 228 into the aorta 230 and is made to emerge at the left femoral artery through an endoluminal exit point. Once the guidewire 220 is positioned, the endoluminal entry or exit port is dilated to permit entry of a catheter therethrough. A protective sheath may be advanced in the venous area to protect the vascular structure.

Figure 26:
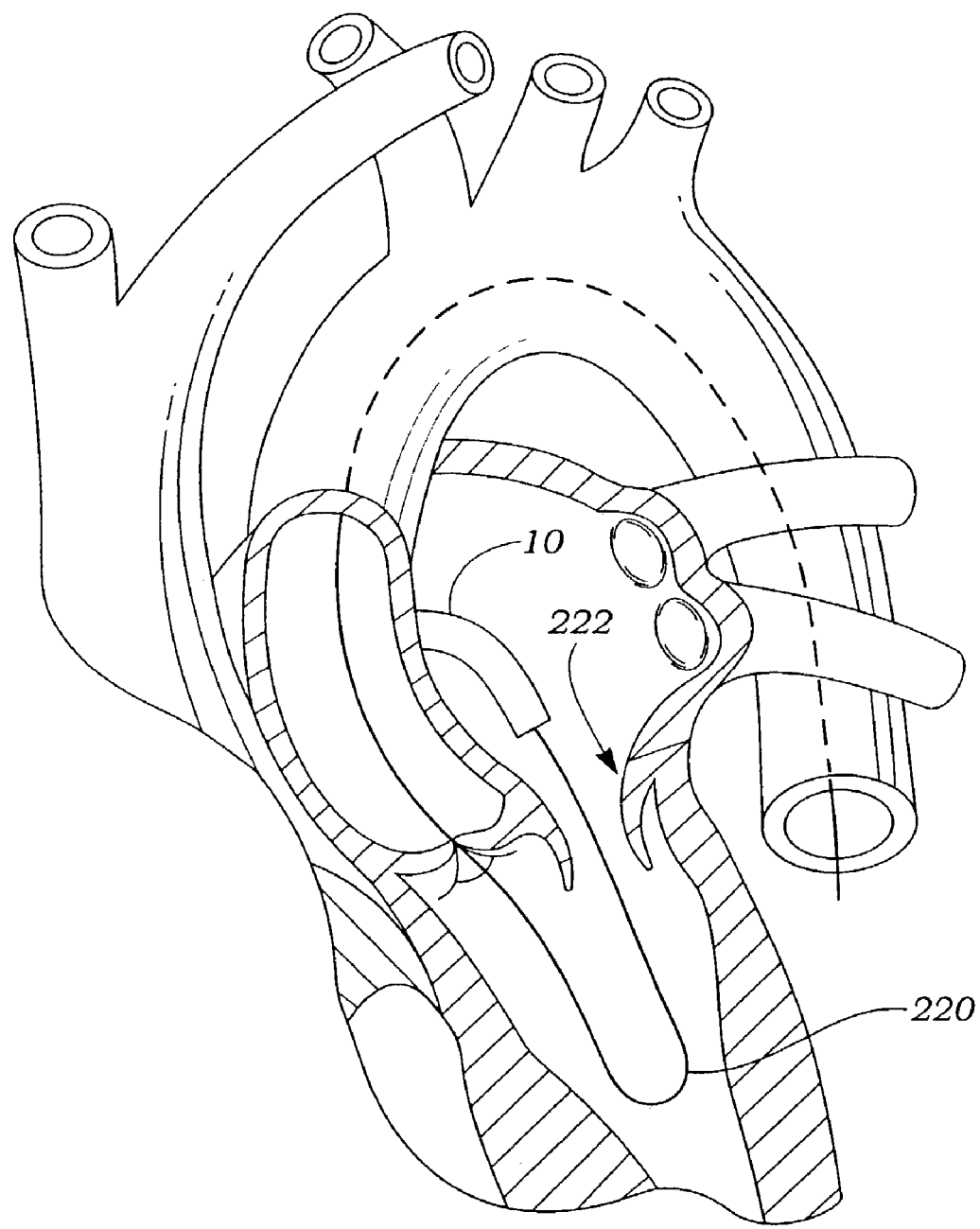
FIG. 26 shows a perspective view of a guide catheter positioned proximate to the mitral valve within a heart.
Figure 27:
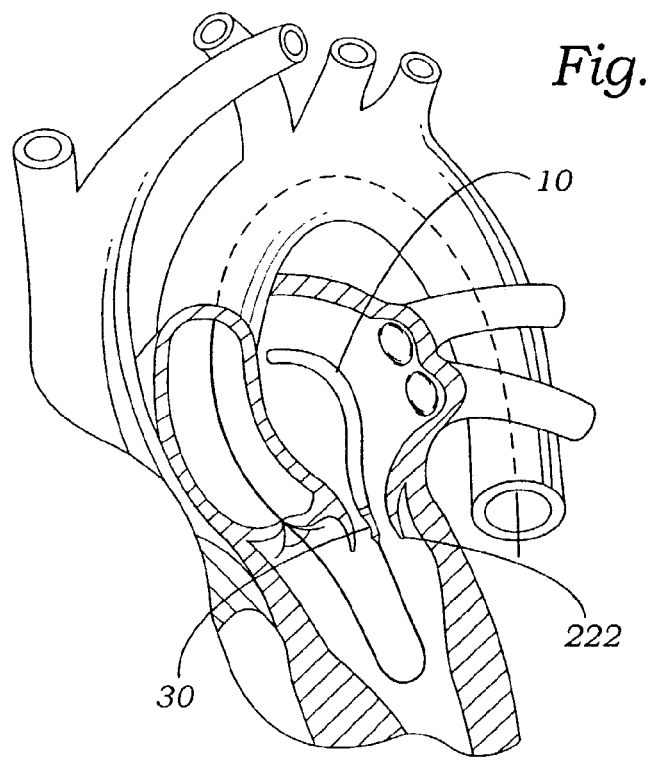
FIG. 27 shows a perspective view of a therapy catheter advancing through a guide catheter to a position proximate to the mitral valve of a heart.
Figure 28:
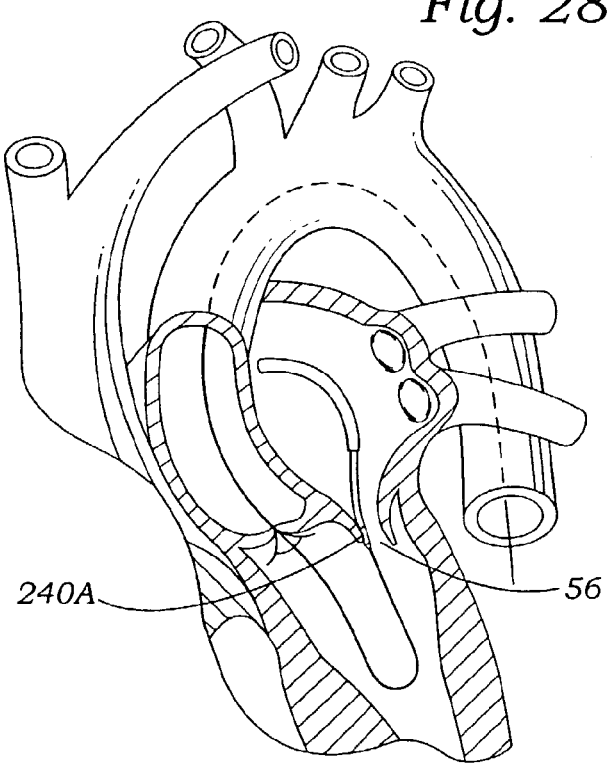
FIG. 28 shows a perspective view of a therapy catheter stabilizing a first leaflet of the mitral valve of a heart.
Figure 29:
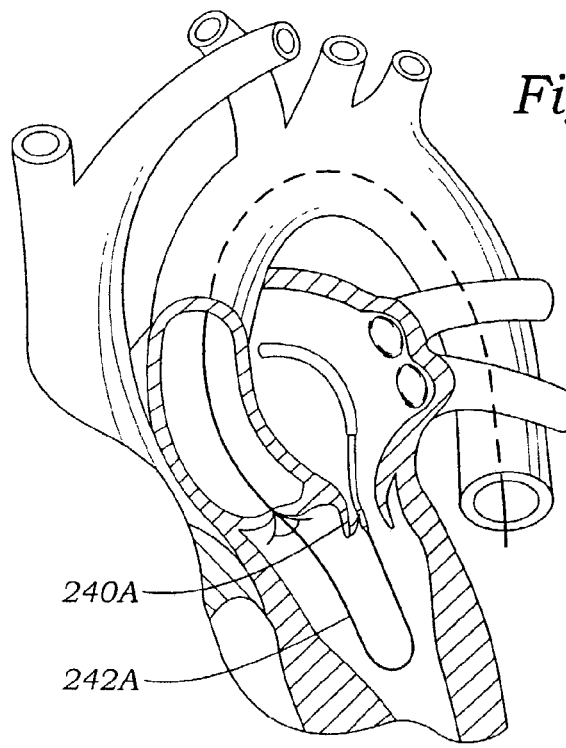
FIG. 29 shows a perspective view of the first leaflet of the mitral valve having a suture applied thereto.
Figure 30:
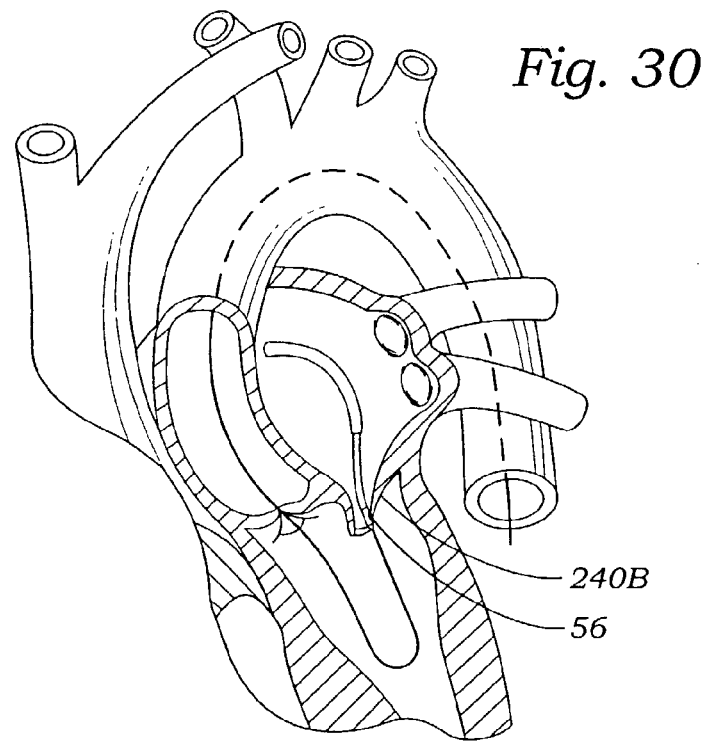
FIG. 30 shows a perspective view of a therapy catheter stabilizing a second leaflet of the mitral valve of a heart.
Figure 31:
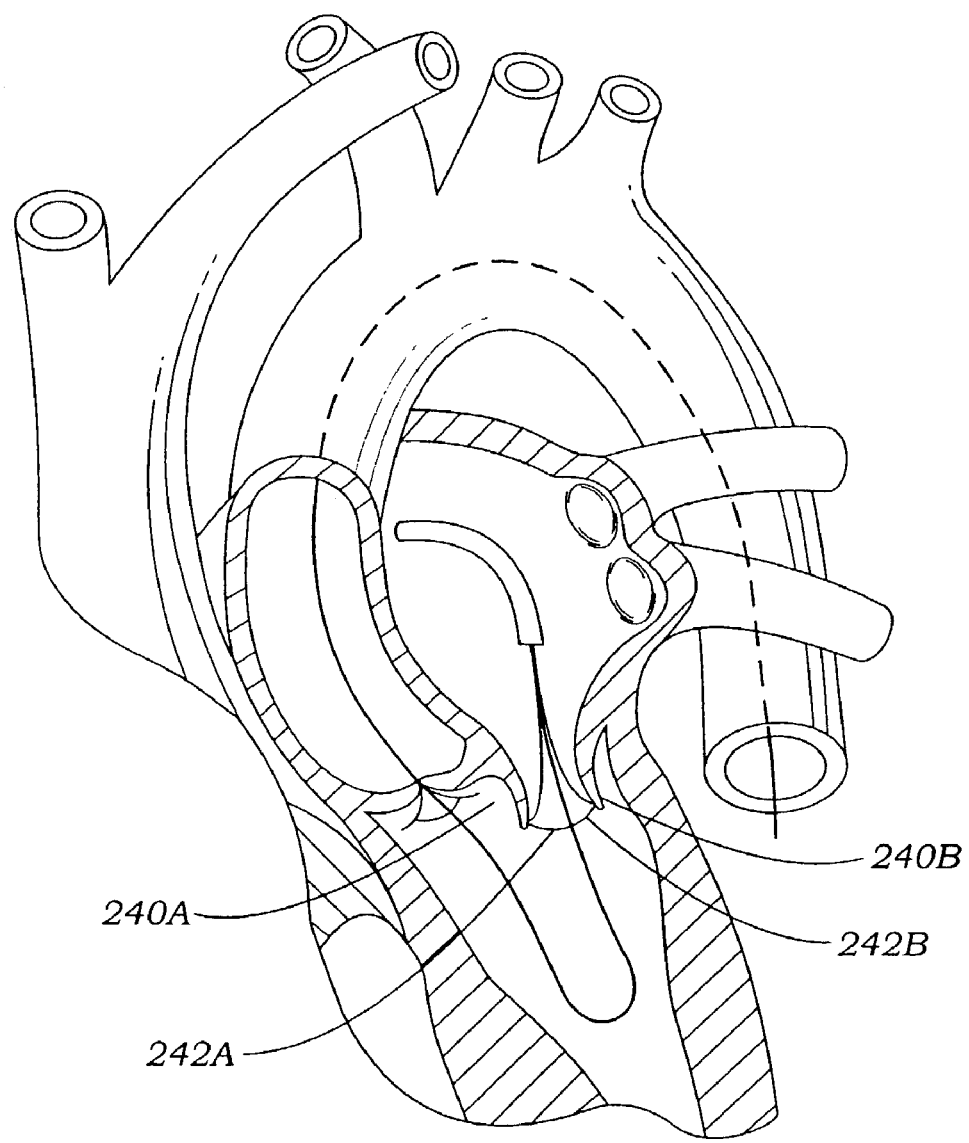
FIG. 31 shows a perspective view of the first and second leaflets of the mitral valve having sutures applied thereto.

As shown in FIG. 26, the guide catheter 10 of the present invention may be attached to the guidewire 220 and advanced through the dilated guidewire entry port to a point proximate to the mitral valve 222. Those skilled in the art will appreciate that the mitral valve repair system of the present invention may approach the mitral valve from an antegrade position or from a retrograde position as desired by the user. Once the guide catheter is suitably positioned in the heart, the therapy catheter 30 may be advanced through the guide catheter 10 to a position proximate to the mitral valve 222. FIG. 27 shows the therapy catheter 30 emerging from the guide catheter 10 proximate to the mitral valve 222. Thereafter, the user may actuate the suction actuator 52 located on the handle body 38 of the therapy device handle 34 (FIG. 6). As a result, a suction force is applied from the suction recess 56 formed on the suture attachment tip 36 of the therapy catheter 30 (FIG. 7) to the tissue located proximate thereto. As shown in FIG. 28, a first valve leaflet 240A is engaged and retained by the suction force applied through the suction recess 56. With the first valve leaflet 240A stabilized, the user may apply a suture 242A thereto as described above. To apply the first suture to the first valve leaflet 240A, the user actuates the first actuator 44 located on the therapy device handle 34, which results in the first needle 70 advancing through the first valve leaflet 240A and engaging and retaining the first needle catch 88A, thereby applying a first suture 242A to the tissue (FIGS. 6-7). Thereafter, the user may terminate application of suction force to the first valve leaflet 240A thereby releasing the sutured tissue. FIG. 29 shows the first valve leaflet 240A having a first suture 242A applied thereto. As shown in FIG. 30, the therapy catheter 30 may then be rotated and positioned to engage a second valve leaflet 240B. Once again, the user may actuate the suction actuator 52 to apply suction force to the second valve leaflet 240B through the suction recess 56. With the second valve leaflet 240B stabilized as shown in FIG. 30, the user may apply a suture 242B thereto by actuating the second actuator 48 located on the therapy device handle 34, which results in the second needle 74 advancing through the second valve leaflet 240B and engaging and retaining the second needle catch 88B, thereby applying a second suture 242B to the tissue. As shown in FIG. 31, the user may terminate the application of suction to the stabilized tissue and remove the therapy catheter from the patient, thereby leaving the first and second sutures 242A, 242B attached to the first and second valve leaflets 240A, 240B. Note that first and second sutures 242A and 242B are actually portions of the same suture such that when the therapy catheter is removed there is a single suture loop through the valve leaflets 240A and 240B.

Figure 32:
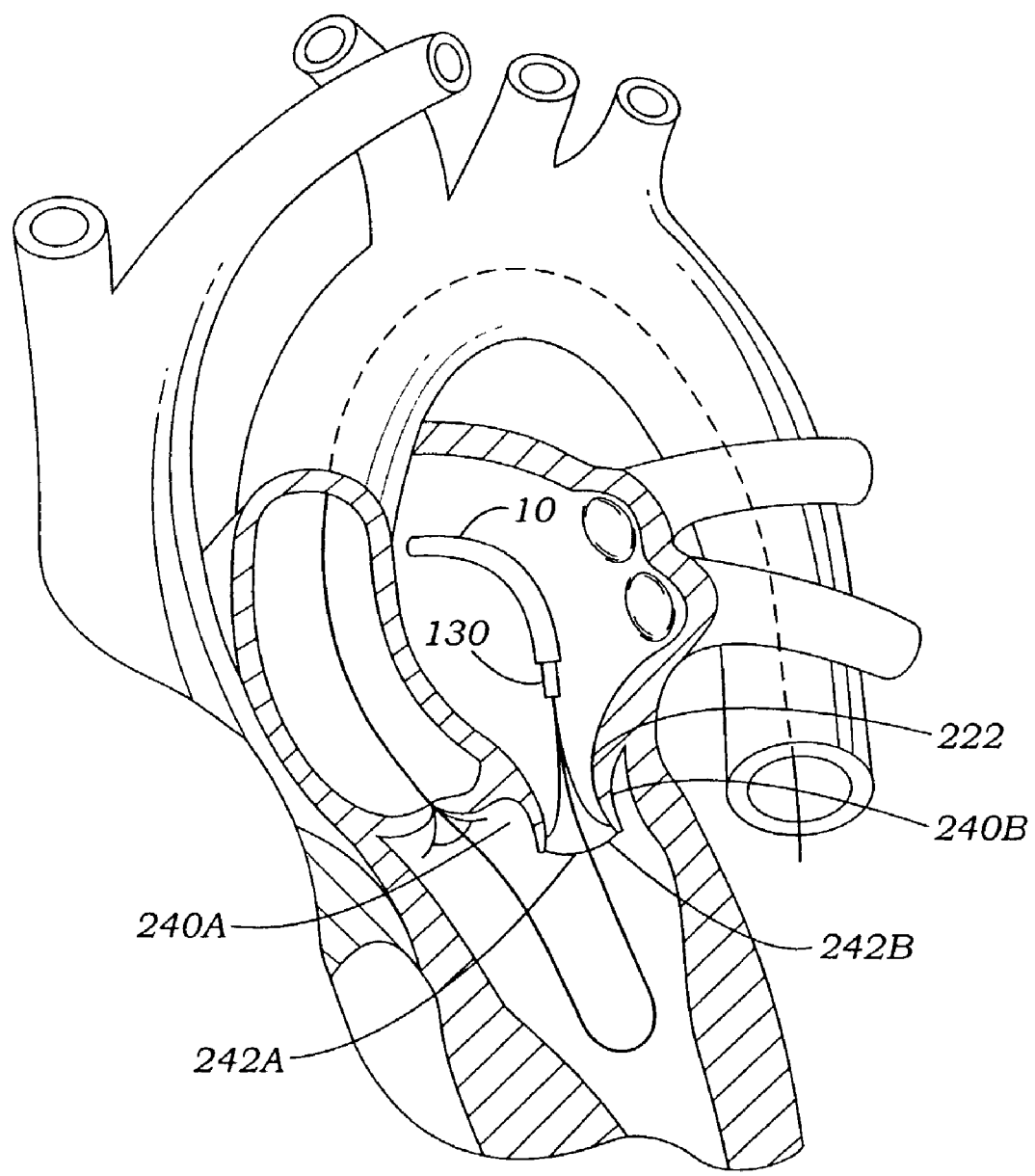
FIG. 32 shows a perspective view of a fastener catheter advancing through a guide catheter to a position proximate to the mitral valve of a heart.
Figure 33:
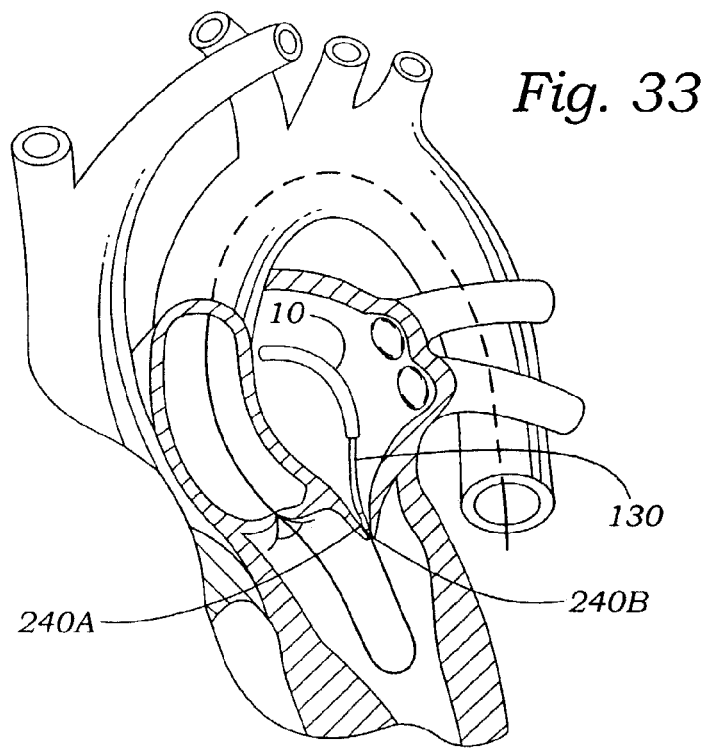
FIG. 33 shows a perspective view of the fastener catheter of the present invention applying a fastener to suture material attached to the mitral valve.
Figure 34:
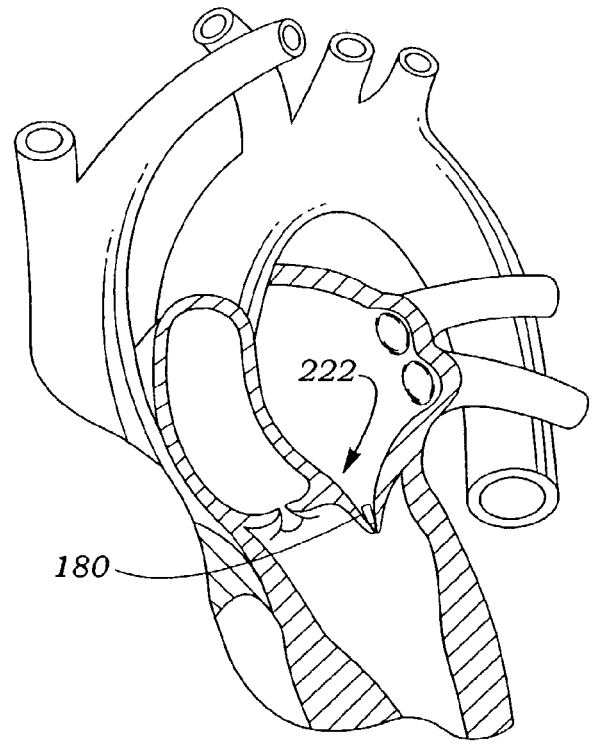
FIG. 34 shows a perspective view of the fastener applied to suture material attached to the first and second leaflet of the mitral valve.

As shown in FIGS. 32-33, the fastener catheter 130 may be attached to the guidewire 220 and will be attached to first and second sutures 242A, 242B. Thereafter, the fastener catheter 130 may be inserted into the guide catheter 10 and advanced to a position proximate to the mitral valve 222. The user then draws the first and second sutures 242A, 242B taut while advancing the fastener catheter 130 to the mitral valve 22, thereby decreasing the distance between the first and second valve leaflets 240A, 240B. The user then actuates the fastener actuator 144 which causes the sleeve 156 to engage and apply the fastener 180 to the first and second sutures 242A, 242B adjacent the leaflets, as described above. Continued actuation of the fastener actuator 144 causes the cutting member 170 to engage and cut the first and second sutures 242A, 242B. As shown in FIG. 34, after the fastener catheter 130, the guide catheter 10, and the guidewire 220 are removed from the patient, the fastener 180 remains applied to the mitral valve 222.

Figure 35:
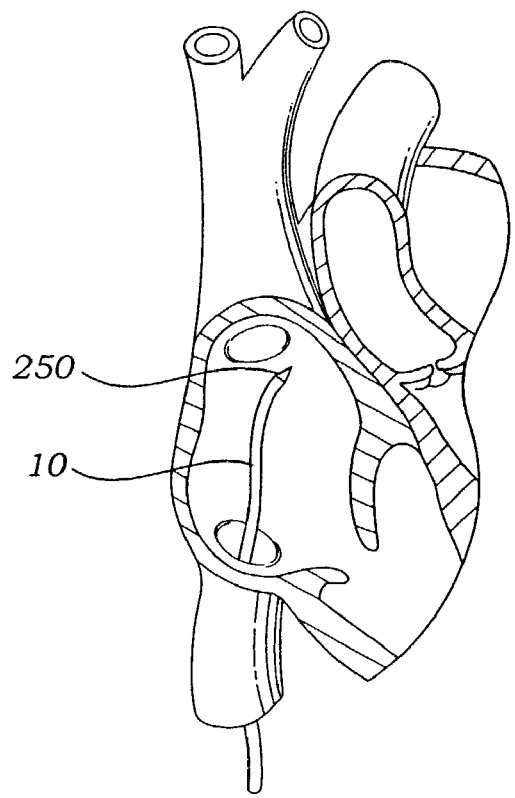
FIG. 35 shows a perspective view of another embodiment of the present invention wherein a dilator is used to introduce the guide catheter onto the left atrium.
Figure 36:
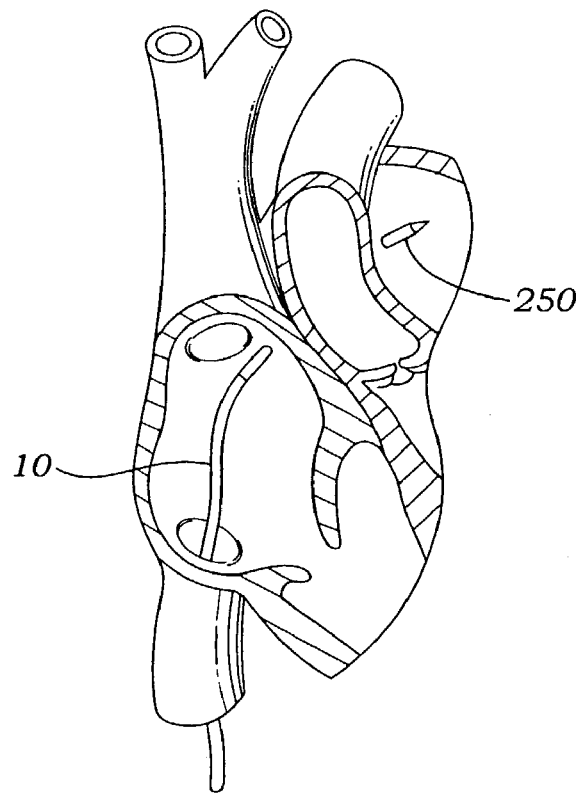
FIG. 36 shows a perspective view of the dilator of the present embodiment traversing the atrial septum.
Figure 37:
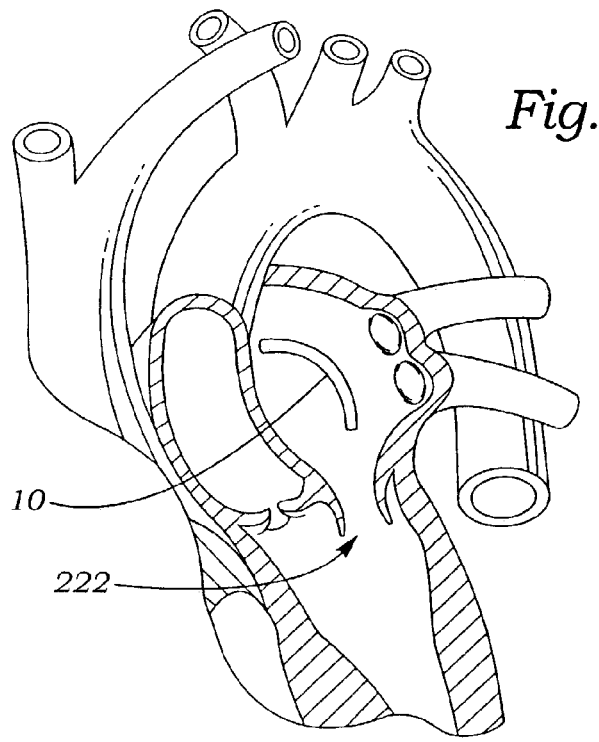
FIG. 37 shows a perspective view of the guide catheter of the present embodiment positioned within the left atrium proximate to the mitral valve.
Figure 38:
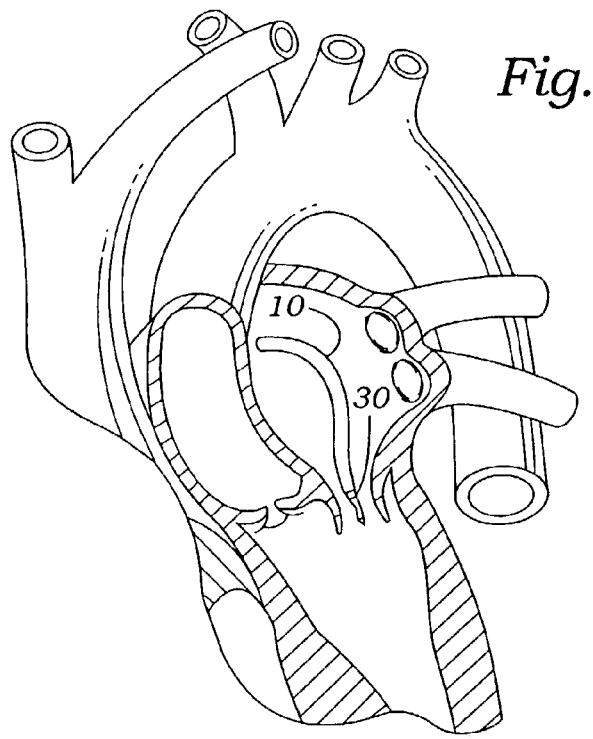
FIG. 38 shows a perspective view of an alternate embodiment of the therapy catheter advanced through the guide catheter to the mitral valve.
Figure 39:
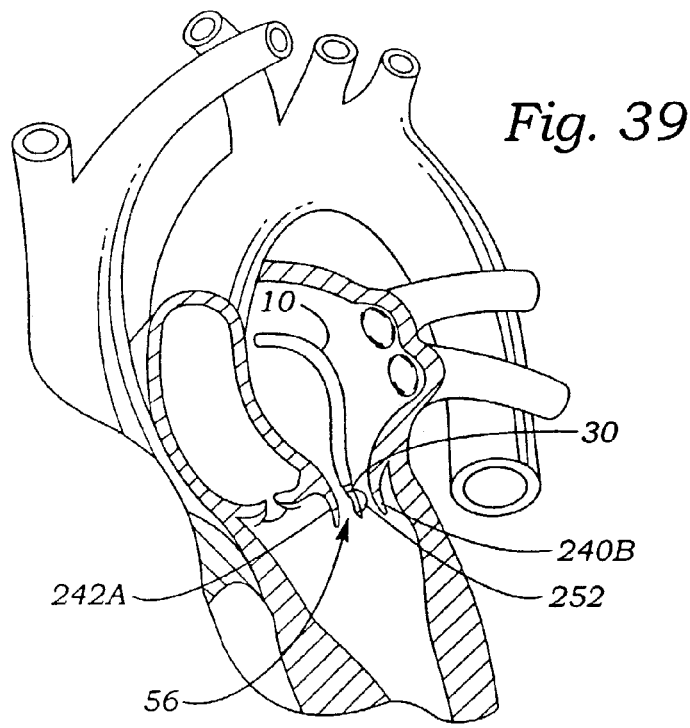
FIG. 39 shows a perspective view of the embodiment of the therapy catheter shown in FIG. 38 having an inflatable positioning balloon positioned thereon inflated.
Figure 40:
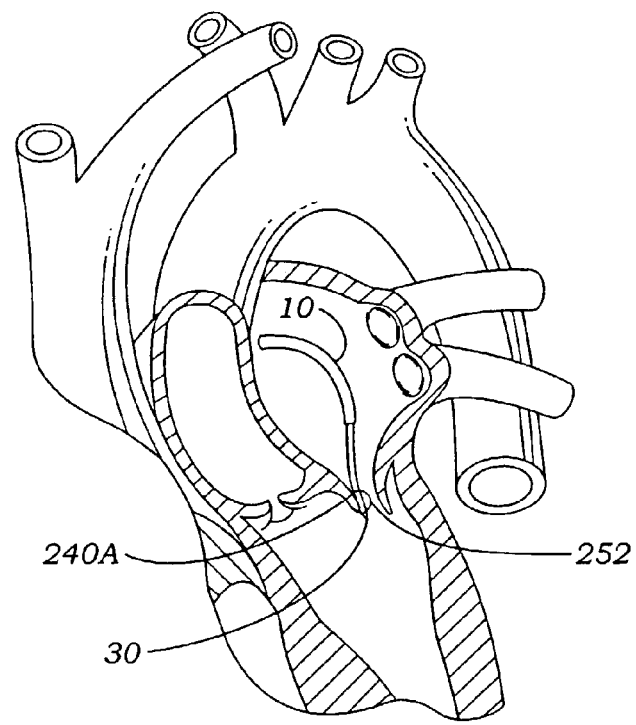
FIG. 40 shows a perspective view of the embodiment of the therapy catheter shown in FIG. 38 engaging a first leaflet.
Figure 41:
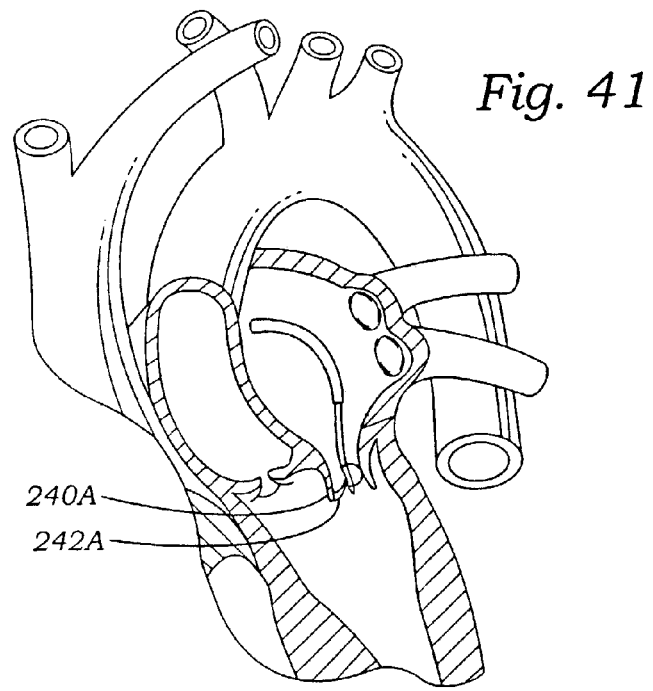
FIG. 41 shows a perspective view of the first leaflet of the mitral valve having a suture attached thereto.
Figure 42:
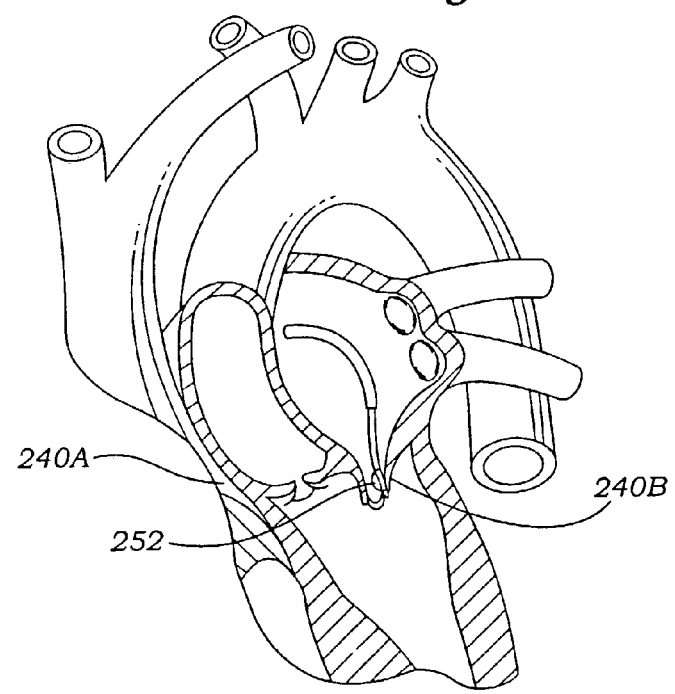
FIG. 42 shows a perspective view of the embodiment of the therapy catheter shown in FIG. 38 engaging the second leaflet of the mitral valve.
Figure 43:
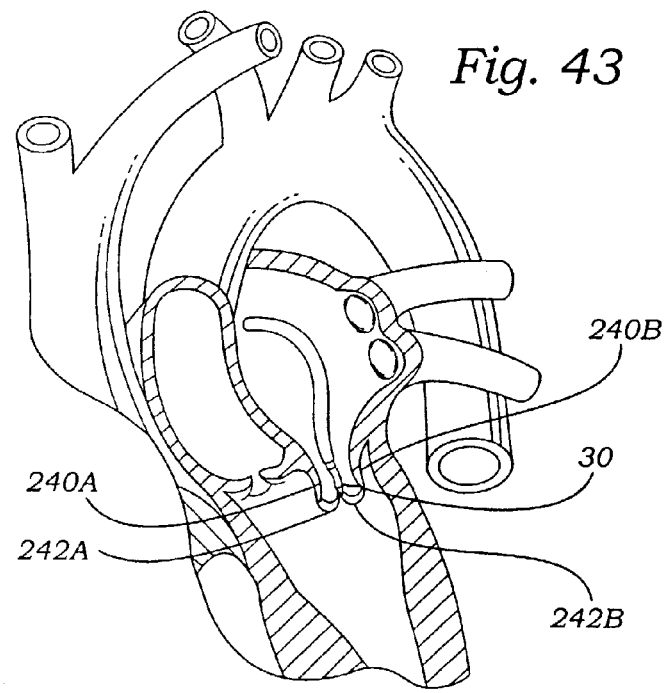
FIG. 43 shows a perspective view of the first and second leaflets of the mitral valve having sutures attached thereto.
Figure 44:
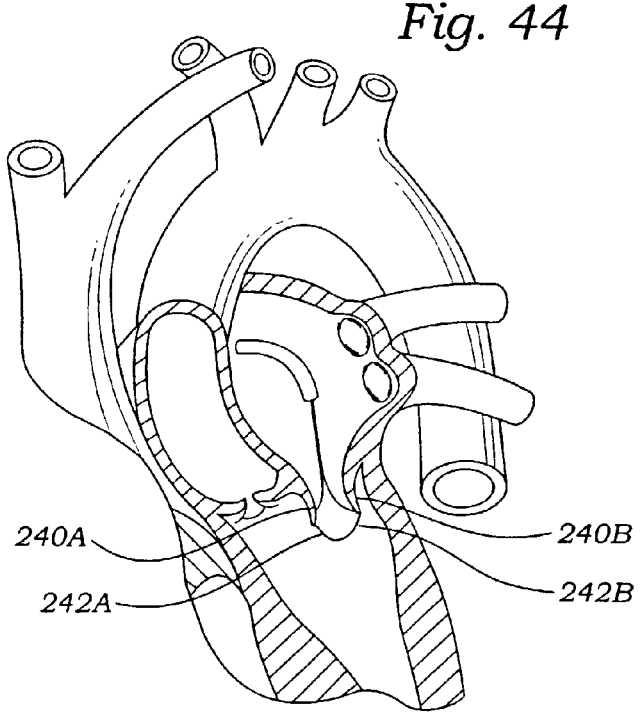
FIG. 44 shows another perspective view of the first and second leaflets of the mitral valve having sutures attached thereto.

FIGS. 35-44 describe an alternate method of repairing tissue, specifically valve leaflets in this embodiment, in vivo. As shown in FIGS. 35-37, a guide catheter 10 is advanced through the circulatory system to the right atrium of the heart. Once positioned, a dilator 250 is advanced through the guide catheter 10 and is made to puncture the atrial septum, thereby entering the left atrium. Thereafter, the guide catheter 10 is advanced into the left atrium through the punctured atrial septum and positioned proximate to the mitral valve 222. As shown in FIG. 38, the therapy catheter 30 may be inserted into the guide catheter 10 and advanced to a position proximate to the mitral valve 222. As shown in FIG. 39, an inflatable positioning balloon 252 (discussed above) located on the therapy catheter 30 is inflated to orient and steady the catheter. The suction actuator 52 on the therapy device handle 34 is then actuated to apply a suction force to the suction recess 56 (see. FIG. 6). The inflated balloon 252 engages the second valve leaflet 240B which forces the suction recess 56 towards the first valve leaflet 240A, thereby resulting in the stabilization of the first valve leaflet 240A as shown in FIG. 40. As shown in FIG. 41, the user may then apply the first suture 242A to the first valve leaflet 240A as described above. Once the suture is applied, the user may deflate the inflatable positioning balloon 252 and rotates the therapy catheter 30 approximately 180°. Thereafter, the user inflates the positioning balloon 252 and actuates suction actuator 52 to apply a suction force to the suction recess 56. As shown in FIG. 42, the inflatable positioning balloon 252 is again inflated and made to engage the first valve leaflet 240 thereby forcing the suction recess 56 to engage the second valve leaflet 240B and permitting the stabilization of the second valve leaflet 240B as shown in FIG. 42. Thereafter, the user applies the second suture 242B to the second valve leaflet 240B as described above. FIGS. 43-44 show the first and second valve leaflets 240A, 240B having a first and second suture 242A, 242B applied thereto. Thereafter, the therapy catheter 30 is removed from the patient's body and the fastener catheter 130 is used to apply a fastener to the first and second sutures 242A, 242B as described above.

In closing, it is understood that the embodiments of the invention disclosed herein are illustrative of the principals of the invention. Other modifications may be employed which remain within the scope of the present invention. Accordingly, the present invention is not limited to the embodiments shown and described in this disclosure.

What is claimed is:

1. A system for repairing tissue within the heart of a patient comprising:
    a guide catheter having a proximal end, a distal end, and an internal lumen formed therein, the internal lumen in fluid communication with the proximal end and the distal end;
    a therapy catheter having a proximal end and a distal end, the distal end having a suction recess disposed thereon, a first needle port and at least one co-aligned and opposing first receiving port thereon, a first needle lumen in communication with the first needle port, the first needle lumen having a first needle therein, a first needle deployment member detachably coupled to the first needle, the first needle and the first needle deployment member positioned within the first needle lumen, the first needle connected to a source of suture material, a first needle trap positioned within the first receiving port, and a first actuator attached to the first needle, the therapy catheter sized to be received axially within the guide catheter wherein the therapy catheter is configured to deploy one or more lines of suture; and
    a fastener catheter having a suture fastener detachably coupled thereto and a cutting member positioned thereon, the fastener catheter sized to be received within the guide catheter, wherein the suture fastener is configured to receive and secure one or more lines of suture, the fastener catheter further comprising a fastener actuator, wherein the fastener actuator is configured to be moved from a first position to a second position and to a third position, wherein the fastener actuator in the first position causes the suture fastener to be maintained securely to the fastener catheter, the fastener actuator in the second position causes deployment of the suture fastener, and the fastener actuator in the third position causes cutting of the one or more lines of suture.

2. The system of claim 1 wherein the therapy catheter further comprises a second needle port and at least one co-aligned and opposing second receiving port thereon, a second needle lumen in communication with the second needle port, the second needle lumen having a second needle therein.

3. The system of claim 2 further comprising a first actuator member in communication with the first needle, and a second actuator member in communication with the second needle, wherein the first actuator member and second actuator member are independently operable.

4. The system of claim 2 wherein the second receiving port further comprises a second needle trap, the second needle trap capable of engaging and retaining the second needle therein.

5. The system of claim 1 wherein the first needle is in communication with a source of suture material.

6. The system of claim 1 wherein the fastener catheter further comprises a fastener lumen formed therein, the fastener lumen capable of receiving a fastener attached to suture material therein.

7. The system of claim 1 wherein the fastener catheter includes a cutting member thereon, the cutting member capable of engaging and cutting suture material.

8. A system for repairing tissue within the heart of a patient, comprising:
 a guide catheter having a proximal end, a distal end, and an internal lumen formed therein, the internal lumen in fluid communication with the proximal end and the distal end;
 a therapy catheter having a proximal end and a distal end, the distal end having a suction recess disposed on a first side thereof whereby the distal end is configured with a suction recess-free surface on an opposite side thereof, a first needle port and at least one co-aligned and opposing first receiving port thereon, a first needle lumen in communication with the first needle port, the first needle lumen having a first needle therein, wherein the first receiving port further comprises a first needle catch, the first needle catch capable of engaging and coupling to the first needle, the therapy catheter sized to be received axially within the guide catheter, wherein the therapy catheter is configured to deploy one or more lines of suture; and
 a fastener catheter having a suture fastener detachably coupled thereto and a cutting member positioned thereon, the fastener catheter sized to be received within the guide catheter, wherein the suture fastener is configured to receive and secure one or more lines of suture, the fastener catheter further comprising a fastener actuator, wherein the fastener actuator is configured to be moved from a first position to a second position and to a third position, wherein the fastener actuator in the first position causes the suture fastener to be maintained securely tote fastener catheter, the fastener actuator in the second position causes deployment of the suture fastener, and the fastener actuator in the third position causes cutting of the one or more lines of suture.

9. The system of claim 8, wherein the suture fastener comprises a fastener inner lumen configured to receive one or more suture lines therein, the suture fastener further comprising one or more fastener engagement elements configured to engage against suture passing through the fastener inner lumen.

10. The system of claim 9, wherein the fastener catheter comprises a generally cylindrical distal end configured to pass within the fastener inner lumen and configured to be engaged against by one or more of the fastener engagement elements.

* * * * *